US012624383B2

(12) United States Patent
De Wijn et al.

(10) Patent No.: US 12,624,383 B2
(45) Date of Patent: May 12, 2026

(54) KINASE ACTIVITY SIGNATURES FOR PREDICTING THE RESPONSE OF NON-SMALL-CELL LUNG CARCINOMA PATIENTS TO A PD-1 OR PD-L1 IMMUNE CHECKPOINT INHIBITOR

(71) Applicant: PAMGENE BV, s-Hertogenbosch (NL)

(72) Inventors: Richard De Wijn, Nijmegen (NL); Dirgje Maria Adriana Van Den Heuvel, Utrecht (NL)

(73) Assignee: PAMGENE BV, 's-Hertogenbosch (NL)

( * ) Notice: Subject to any disclaimer, the term of this patent is extended or adjusted under 35 U.S.C. 154(b) by 898 days.

(21) Appl. No.: 17/636,597

(22) PCT Filed: Sep. 4, 2020

(86) PCT No.: PCT/EP2020/074703
§ 371 (c)(1),
(2) Date: Feb. 18, 2022

(87) PCT Pub. No.: WO2021/043953
PCT Pub. Date: Mar. 11, 2021

(65) Prior Publication Data
US 2022/0298538 A1        Sep. 22, 2022

(30) Foreign Application Priority Data
Sep. 5, 2019    (EP) ..................................... 19195591

(51) Int. Cl.
*C12Q 1/48*        (2006.01)
(52) U.S. Cl.
CPC ................................... *C12Q 1/485* (2013.01)
(58) Field of Classification Search
CPC ................................................... C12Q 1/485
See application file for complete search history.

(56) References Cited

U.S. PATENT DOCUMENTS

| | | |
|---|---|---|
| 8,962,267 B1 | 2/2015 | De Wijn et al. |
| 2004/0127453 A1 | 7/2004 | Lyons et al. |
| 2006/0019284 A1 | 1/2006 | Huang et al. |
| 2006/0140947 A1 | 6/2006 | Lyons et al. |
| 2007/0129360 A1 | 6/2007 | Phamidipati et al. |
| 2007/0129362 A1 | 6/2007 | Bhamidipati et al. |
| 2007/0129630 A1 | 6/2007 | Shimko |
| 2013/0230511 A1 | 9/2013 | Heymach et al. |
| 2016/0303124 A1 | 10/2016 | Webster et al. |
| 2018/0200378 A1 | 7/2018 | Bennett et al. |
| 2020/0024669 A1 | 1/2020 | Spetzler et al. |
| 2020/0215199 A1 | 7/2020 | Bennett et al. |
| 2020/0232043 A1 | 7/2020 | Ruijtenbeek et al. |

FOREIGN PATENT DOCUMENTS

| | | | |
|---|---|---|---|
| EP | 2239579 A1 | 10/2010 | |
| WO | 2003065995 A2 | 8/2003 | |
| WO | 2006005035 A2 | 1/2006 | |
| WO | 2010020619 A2 | 2/2010 | |
| WO | WO-2017167942 A1 * | 10/2017 | ............. C12Q 1/485 |
| WO | 2018127699 A1 | 7/2018 | |
| WO | 2018175501 A1 | 9/2018 | |
| WO | 2019018218 A1 | 1/2019 | |
| WO | 2019030311 A1 | 2/2019 | |

OTHER PUBLICATIONS

Shibuya M. Tyrosine Kinase Receptor Flt/VEGFR Family: Its Characterization Related to Angiogenesis and Cancer. Genes Cancer. Nov. 2010;1(11):1119-23. doi: 10.1177/1947601910392987. PMID: 21779435; PMCID: PMC3092272. (Year: 2010).*
Reungwetwattana T, Dy GK. Targeted therapies in development for non-small cell lung cancer. J Carcinog. Dec. 31, 2013;12:22. doi: 10.4103/1477-3163.123972. PMID: 24574860; PMCID: PMC3927069. (Year: 2013).*
Lim SH, Kim SY, Kim K, Jang H, Ahn S, Kim KM, Kim NK, Park W, Lee SJ, Kim ST, Park SH, Park JO, Park YS, Lee SH, Lim HY, Park K, Kang WK, Lee J. The implication of FLT3 amplification for FLT targeted therapeutics in solid tumors. Oncotarget. Jan. 10, 2017;8(2):3237-3245. doi: 10.18632/oncotarget.13700. (Year: 2017).*
El-Gamal MI, Mewafi NH, Abdelmotteleb NE, Emara MA, Tarazi H, Sbenati RM, Madkour MM, Zaraei SO, Shahin AI, Anbar HS. A Review of HER4 (ErbB4) Kinase, Its Impact on Cancer, and Its Inhibitors. Molecules. Dec. 5, 2021;26(23):7376. doi: 10.3390/molecules26237376. PMID: 34885957; PMCID: PMC8659013. (Year: 2021).*
Noé, Gaëlle, et al. "Differential kinase activation in peripheral blood mononuclear cells from non-small-cell lung cancer patients treated with nivolumab." Cancers 11.6 (2019): 762. (Year: 2019).*
International Search Report and Written Opinion issued in PCT Application No. PCT/EP2020/074703, dated Oct. 26, 2020, 17 pp.
European Patent Office, Extended European Search Report issued in EPO Application No. 19195591.3, dated Mar. 3, 2020, 11 pp.

* cited by examiner

*Primary Examiner* — Robert J Yamasaki
(74) *Attorney, Agent, or Firm* — Amster, Rothstein & Ebenstein LLP

(57)        ABSTRACT

The present invention relates to a method for determining or predicting the response of a patient diagnosed with non-small-cell lung carcinoma a PD-1 or PD-L1 immune checkpoint inhibitor. The present invention also aims to provide methods and devices for predicting the response of patients diagnosed with non-small-cell lung carcinoma to PD-1 or PD-L1 immune checkpoint inhibitors. More specifically, the present invention provides methods which measure kinase-activity and profiles and inhibitions thereof by drugs in blood samples of said patients.

9 Claims, 7 Drawing Sheets
Specification includes a Sequence Listing.

A

B

SEQUENCE LISTING

```
<160> NUMBER OF SEQ ID NOS: 93

<210> SEQ ID NO 1
<211> LENGTH: 13
<212> TYPE: PRT
<213> ORGANISM: Artificial Sequence
<220> FEATURE:
<223> OTHER INFORMATION: 41_654_666

<400> SEQUENCE: 1

Leu Asp Gly Glu Asn Ile Tyr Ile Arg His Ser Asn Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: ACHD_383_395

<400> SEQUENCE: 2

Tyr Ile Ser Lys Ala Glu Glu Tyr Phe Leu Leu Lys Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: ANXA1_14_26

<400> SEQUENCE: 3

Ile Glu Asn Glu Glu Gln Glu Tyr Val Gln Thr Val Lys
```

-continued

```
1              5                    10
```

<210> SEQ ID NO 4
<211> LENGTH: 13
<212> TYPE: PRT
<213> ORGANISM: Artificial Sequence
<220> FEATURE:
<223> OTHER INFORMATION: ANXA2_17_29

<400> SEQUENCE: 4

```
His Ser Thr Pro Pro Ser Ala Tyr Gly Ser Val Lys Ala
1              5                    10
```

<210> SEQ ID NO 5
<211> LENGTH: 13
<212> TYPE: PRT
<213> ORGANISM: Artificial Sequence
<220> FEATURE:
<223> OTHER INFORMATION: B3AT_39_51

<400> SEQUENCE: 5

```
Thr Glu Ala Thr Ala Thr Asp Tyr His Thr Thr Ser His
1              5                    10
```

<210> SEQ ID NO 6
<211> LENGTH: 13
<212> TYPE: PRT
<213> ORGANISM: Artificial Sequence
<220> FEATURE:
<223> OTHER INFORMATION: CTNB1_79_91

<400> SEQUENCE: 6

```
Val Ala Asp Ile Asp Gly Gln Tyr Ala Met Thr Arg Ala
1              5                    10
```

<210> SEQ ID NO 7
<211> LENGTH: 15
<212> TYPE: PRT
<213> ORGANISM: Artificial Sequence
<220> FEATURE:
<223> OTHER INFORMATION: PGFRB_1014_1028

<400> SEQUENCE: 7

```
Pro Asn Glu Gly Asp Asn Asp Tyr Ile Ile Pro Leu Pro Asp Pro
1              5                    10                  15
```

<210> SEQ ID NO 8
<211> LENGTH: 13
<212> TYPE: PRT
<213> ORGANISM: Artificial Sequence
<220> FEATURE:
<223> OTHER INFORMATION: CALM_95_107

<400> SEQUENCE: 8

```
Lys Asp Gly Asn Gly Tyr Ile Ser Ala Ala Glu Leu Arg
1              5                    10
```

<210> SEQ ID NO 9
<211> LENGTH: 13
<212> TYPE: PRT
<213> ORGANISM: Artificial Sequence
<220> FEATURE:
<223> OTHER INFORMATION: CBL_693_705

<400> SEQUENCE: 9

```
Glu Gly Glu Glu Asp Thr Glu Tyr Met Thr Pro Ser Ser
1              5                    10
```

-continued

```
<210> SEQ ID NO 10
<211> LENGTH: 13
<212> TYPE: PRT
<213> ORGANISM: Artificial Sequence
<220> FEATURE:
<223> OTHER INFORMATION: CD3Z_116_128

<400> SEQUENCE: 10

Lys Asp Lys Met Ala Glu Ala Tyr Ser Glu Ile Gly Met
1               5                   10

<210> SEQ ID NO 11
<211> LENGTH: 13
<212> TYPE: PRT
<213> ORGANISM: Artificial Sequence
<220> FEATURE:
<223> OTHER INFORMATION: CD3Z_146_158

<400> SEQUENCE: 11

Ser Thr Ala Thr Lys Asp Thr Tyr Asp Ala Leu His Met
1               5                   10

<210> SEQ ID NO 12
<211> LENGTH: 13
<212> TYPE: PRT
<213> ORGANISM: Artificial Sequence
<220> FEATURE:
<223> OTHER INFORMATION: CDK7_157_169

<400> SEQUENCE: 12

Gly Leu Ala Lys Ser Phe Gly Ser Pro Asn Arg Ala Tyr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: CRK_214_226

<400> SEQUENCE: 13

Gly Pro Pro Glu Pro Gly Pro Tyr Ala Gln Pro Ser Val
1               5                   10

<210> SEQ ID NO 14
<211> LENGTH: 13
<212> TYPE: PRT
<213> ORGANISM: Artificial Sequence
<220> FEATURE:
<223> OTHER INFORMATION: DCX_109_121

<400> SEQUENCE: 14

Gly Ile Val Tyr Ala Val Ser Ser Asp Arg Phe Arg Ser
1               5                   10

<210> SEQ ID NO 15
<211> LENGTH: 13
<212> TYPE: PRT
<213> ORGANISM: Artificial Sequence
<220> FEATURE:
<223> OTHER INFORMATION: DDR1_506_518

<400> SEQUENCE: 15

Leu Leu Leu Ser Asn Pro Ala Tyr Arg Leu Leu Leu Ala
1               5                   10
```

-continued

```
<210> SEQ ID NO 16
<211> LENGTH: 13
<212> TYPE: PRT
<213> ORGANISM: Artificial Sequence
<220> FEATURE:
<223> OTHER INFORMATION: DYR1A_212_224

<400> SEQUENCE: 16

Lys His Asp Thr Glu Met Lys Tyr Tyr Ile Val His Leu
1               5                   10

<210> SEQ ID NO 17
<211> LENGTH: 13
<212> TYPE: PRT
<213> ORGANISM: Artificial Sequence
<220> FEATURE:
<223> OTHER INFORMATION: DYR1A_312_324

<400> SEQUENCE: 17

Cys Gln Leu Gly Gln Arg Ile Tyr Gln Tyr Ile Gln Ser
1               5                   10

<210> SEQ ID NO 18
<211> LENGTH: 13
<212> TYPE: PRT
<213> ORGANISM: Artificial Sequence
<220> FEATURE:
<223> OTHER INFORMATION: EGFR_1103_1115

<400> SEQUENCE: 18

Gly Ser Val Gln Asn Pro Val Tyr His Asn Gln Pro Leu
1               5                   10

<210> SEQ ID NO 19
<211> LENGTH: 13
<212> TYPE: PRT
<213> ORGANISM: Artificial Sequence
<220> FEATURE:
<223> OTHER INFORMATION: EGFR_1118_1130

<400> SEQUENCE: 19

Ala Pro Ser Arg Asp Pro His Tyr Gln Asp Pro His Ser
1               5                   10

<210> SEQ ID NO 20
<211> LENGTH: 13
<212> TYPE: PRT
<213> ORGANISM: Artificial Sequence
<220> FEATURE:
<223> OTHER INFORMATION: EGFR_1165_1177

<400> SEQUENCE: 20

Ile Ser Leu Asp Asn Pro Asp Tyr Gln Gln Asp Phe Phe
1               5                   10

<210> SEQ ID NO 21
<211> LENGTH: 13
<212> TYPE: PRT
<213> ORGANISM: Artificial Sequence
<220> FEATURE:
<223> OTHER INFORMATION: EGFR_1190_1202

<400> SEQUENCE: 21

Ser Thr Ala Glu Asn Ala Glu Tyr Leu Arg Val Ala Pro
1               5                   10
```

-continued

```
<210> SEQ ID NO 22
<211> LENGTH: 13
<212> TYPE: PRT
<213> ORGANISM: Artificial Sequence
<220> FEATURE:
<223> OTHER INFORMATION: EPHA1_774_786

<400> SEQUENCE: 22

Leu Asp Asp Phe Asp Gly Thr Tyr Glu Thr Gln Gly Gly
1               5                   10

<210> SEQ ID NO 23
<211> LENGTH: 13
<212> TYPE: PRT
<213> ORGANISM: Artificial Sequence
<220> FEATURE:
<223> OTHER INFORMATION: EPHA4_589_601

<400> SEQUENCE: 23

Leu Asn Gln Gly Val Arg Thr Tyr Val Asp Pro Phe Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: EPHA7_607_619

<400> SEQUENCE: 24

Thr Tyr Ile Asp Pro Glu Thr Tyr Glu Asp Pro Asn Arg
1               5                   10

<210> SEQ ID NO 25
<211> LENGTH: 13
<212> TYPE: PRT
<213> ORGANISM: Artificial Sequence
<220> FEATURE:
<223> OTHER INFORMATION: EPHB1_771_783

<400> SEQUENCE: 25

Asp Asp Thr Ser Asp Pro Thr Tyr Thr Ser Ser Leu Gly
1               5                   10

<210> SEQ ID NO 26
<211> LENGTH: 13
<212> TYPE: PRT
<213> ORGANISM: Artificial Sequence
<220> FEATURE:
<223> OTHER INFORMATION: EPHB4_583_595

<400> SEQUENCE: 26

Ile Gly His Gly Thr Lys Val Tyr Ile Asp Pro Phe Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: EPOR_361_373

<400> SEQUENCE: 27

Ser Glu His Ala Gln Asp Thr Tyr Leu Val Leu Asp Lys
1               5                   10

<210> SEQ ID NO 28
```

```
<211> LENGTH: 13
<212> TYPE: PRT
<213> ORGANISM: Artificial Sequence
<220> FEATURE:
<223> OTHER INFORMATION: EPOR_419_431

<400> SEQUENCE: 28

Ala Ser Ala Ala Ser Phe Glu Tyr Thr Ile Leu Asp Pro
1               5                   10

<210> SEQ ID NO 29
<211> LENGTH: 13
<212> TYPE: PRT
<213> ORGANISM: Artificial Sequence
<220> FEATURE:
<223> OTHER INFORMATION: ERBB2_1241_1253

<400> SEQUENCE: 29

Pro Thr Ala Glu Asn Pro Glu Tyr Leu Gly Leu Asp Val
1               5                   10

<210> SEQ ID NO 30
<211> LENGTH: 13
<212> TYPE: PRT
<213> ORGANISM: Artificial Sequence
<220> FEATURE:
<223> OTHER INFORMATION: ERBB2_870_882

<400> SEQUENCE: 30

Leu Asp Ile Asp Glu Thr Glu Tyr His Ala Asp Gly Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: ERBB4_1181_1193

<400> SEQUENCE: 31

Gln Ala Leu Asp Asn Pro Glu Tyr His Asn Ala Ser Asn
1               5                   10

<210> SEQ ID NO 32
<211> LENGTH: 13
<212> TYPE: PRT
<213> ORGANISM: Artificial Sequence
<220> FEATURE:
<223> OTHER INFORMATION: ERBB4_1277_1289

<400> SEQUENCE: 32

Ile Val Ala Glu Asn Pro Glu Tyr Leu Ser Glu Phe Ser
1               5                   10

<210> SEQ ID NO 33
<211> LENGTH: 13
<212> TYPE: PRT
<213> ORGANISM: Artificial Sequence
<220> FEATURE:
<223> OTHER INFORMATION: FAK1_569_581

<400> SEQUENCE: 33

Arg Tyr Met Glu Asp Ser Thr Tyr Tyr Lys Ala Ser Lys
1               5                   10

<210> SEQ ID NO 34
<211> LENGTH: 13
```

-continued

```
<212> TYPE: PRT
<213> ORGANISM: Artificial Sequence
<220> FEATURE:
<223> OTHER INFORMATION: FAK2_572_584

<400> SEQUENCE: 34

Arg Tyr Ile Glu Asp Glu Asp Tyr Tyr Lys Ala Ser Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: FER_707_719

<400> SEQUENCE: 35

Arg Gln Glu Asp Gly Gly Val Tyr Ser Ser Ser Gly Leu
1               5                   10

<210> SEQ ID NO 36
<211> LENGTH: 13
<212> TYPE: PRT
<213> ORGANISM: Artificial Sequence
<220> FEATURE:
<223> OTHER INFORMATION: FES_706_718

<400> SEQUENCE: 36

Arg Glu Glu Ala Asp Gly Val Tyr Ala Ala Ser Gly Gly
1               5                   10

<210> SEQ ID NO 37
<211> LENGTH: 13
<212> TYPE: PRT
<213> ORGANISM: Artificial Sequence
<220> FEATURE:
<223> OTHER INFORMATION: FGFR1_761_773

<400> SEQUENCE: 37

Thr Ser Asn Gln Glu Tyr Leu Asp Leu Ser Met Pro Leu
1               5                   10

<210> SEQ ID NO 38
<211> LENGTH: 13
<212> TYPE: PRT
<213> ORGANISM: Artificial Sequence
<220> FEATURE:
<223> OTHER INFORMATION: FGFR2_762_774

<400> SEQUENCE: 38

Thr Leu Thr Thr Asn Glu Glu Tyr Leu Asp Leu Ser Gln
1               5                   10

<210> SEQ ID NO 39
<211> LENGTH: 13
<212> TYPE: PRT
<213> ORGANISM: Artificial Sequence
<220> FEATURE:
<223> OTHER INFORMATION: FGFR3_753_765

<400> SEQUENCE: 39

Thr Val Thr Ser Thr Asp Glu Tyr Leu Asp Leu Ser Ala
1               5                   10

<210> SEQ ID NO 40
<211> LENGTH: 13
<212> TYPE: PRT
```

<213> ORGANISM: Artificial Sequence
<220> FEATURE:
<223> OTHER INFORMATION: INSR_992_1004

<400> SEQUENCE: 40

Tyr Ala Ser Ser Asn Pro Glu Tyr Leu Ser Ala Ser Asp
1               5                   10

<210> SEQ ID NO 41
<211> LENGTH: 13
<212> TYPE: PRT
<213> ORGANISM: Artificial Sequence
<220> FEATURE:
<223> OTHER INFORMATION: JAK1_1015_1027

<400> SEQUENCE: 41

Ala Ile Glu Thr Asp Lys Glu Tyr Tyr Thr Val Lys Asp
1               5                   10

<210> SEQ ID NO 42
<211> LENGTH: 15
<212> TYPE: PRT
<213> ORGANISM: Artificial Sequence
<220> FEATURE:
<223> OTHER INFORMATION: JAK2_563_577

<400> SEQUENCE: 42

Val Arg Arg Glu Val Gly Asp Tyr Gly Gln Leu His Glu Thr Glu
1               5                   10                  15

<210> SEQ ID NO 43
<211> LENGTH: 13
<212> TYPE: PRT
<213> ORGANISM: Artificial Sequence
<220> FEATURE:
<223> OTHER INFORMATION: K2C6B_53_65

<400> SEQUENCE: 43

Gly Ala Gly Phe Gly Ser Arg Ser Leu Tyr Gly Leu Gly
1               5                   10

<210> SEQ ID NO 44
<211> LENGTH: 13
<212> TYPE: PRT
<213> ORGANISM: Artificial Sequence
<220> FEATURE:
<223> OTHER INFORMATION: K2C8_425_437

<400> SEQUENCE: 44

Ser Ala Tyr Gly Gly Leu Thr Ser Pro Gly Leu Ser Tyr
1               5                   10

<210> SEQ ID NO 45
<211> LENGTH: 13
<212> TYPE: PRT
<213> ORGANISM: Artificial Sequence
<220> FEATURE:
<223> OTHER INFORMATION: KSYK_518_530

<400> SEQUENCE: 45

Ala Leu Arg Ala Asp Glu Asn Tyr Tyr Lys Ala Gln Thr
1               5                   10

<210> SEQ ID NO 46
<211> LENGTH: 13
<212> TYPE: PRT
<213> ORGANISM: Artificial Sequence -continued

```
<220> FEATURE:
<223> OTHER INFORMATION: LAT_194_206

<400> SEQUENCE: 46

Met Glu Ser Ile Asp Asp Tyr Val Asn Val Pro Glu Ser
1               5                   10

<210> SEQ ID NO 47
<211> LENGTH: 13
<212> TYPE: PRT
<213> ORGANISM: Artificial Sequence
<220> FEATURE:
<223> OTHER INFORMATION: LAT_249_261

<400> SEQUENCE: 47

Glu Glu Gly Ala Pro Asp Tyr Glu Asn Leu Gln Glu Leu
1               5                   10

<210> SEQ ID NO 48
<211> LENGTH: 13
<212> TYPE: PRT
<213> ORGANISM: Artificial Sequence
<220> FEATURE:
<223> OTHER INFORMATION: LCK_387_399

<400> SEQUENCE: 48

Arg Leu Ile Glu Asp Asn Glu Tyr Thr Ala Arg Glu Gly
1               5                   10

<210> SEQ ID NO 49
<211> LENGTH: 13
<212> TYPE: PRT
<213> ORGANISM: Artificial Sequence
<220> FEATURE:
<223> OTHER INFORMATION: MBP_198_210

<400> SEQUENCE: 49

Ala Arg Thr Ala His Tyr Gly Ser Leu Pro Gln Lys Ser
1               5                   10

<210> SEQ ID NO 50
<211> LENGTH: 13
<212> TYPE: PRT
<213> ORGANISM: Artificial Sequence
<220> FEATURE:
<223> OTHER INFORMATION: MET_1227_1239

<400> SEQUENCE: 50

Arg Asp Met Tyr Asp Lys Glu Tyr Tyr Ser Val His Asn
1               5                   10

<210> SEQ ID NO 51
<211> LENGTH: 13
<212> TYPE: PRT
<213> ORGANISM: Artificial Sequence
<220> FEATURE:
<223> OTHER INFORMATION: MK01_180_192

<400> SEQUENCE: 51

His Thr Gly Phe Leu Thr Glu Tyr Val Ala Thr Arg Trp
1               5                   10

<210> SEQ ID NO 52
<211> LENGTH: 13
<212> TYPE: PRT
<213> ORGANISM: Artificial Sequence
<220> FEATURE:
```

-continued

```
<223> OTHER INFORMATION: MK07_211_223

<400> SEQUENCE: 52

Ala Glu His Gln Tyr Phe Met Thr Glu Tyr Val Ala Thr
1               5                   10

<210> SEQ ID NO 53
<211> LENGTH: 13
<212> TYPE: PRT
<213> ORGANISM: Artificial Sequence
<220> FEATURE:
<223> OTHER INFORMATION: MK10_216_228

<400> SEQUENCE: 53

Thr Ser Phe Met Met Thr Pro Tyr Val Val Thr Arg Tyr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: MK12_178_190

<400> SEQUENCE: 54

Ala Asp Ser Glu Met Thr Gly Tyr Val Val Thr Arg Trp
1               5                   10

<210> SEQ ID NO 55
<211> LENGTH: 13
<212> TYPE: PRT
<213> ORGANISM: Artificial Sequence
<220> FEATURE:
<223> OTHER INFORMATION: NTRK2_696_708

<400> SEQUENCE: 55

Gly Met Ser Arg Asp Val Tyr Ser Thr Asp Tyr Tyr Arg
1               5                   10

<210> SEQ ID NO 56
<211> LENGTH: 13
<212> TYPE: PRT
<213> ORGANISM: Artificial Sequence
<220> FEATURE:
<223> OTHER INFORMATION: ODBA_340_352

<400> SEQUENCE: 56

Asp Asp Ser Ser Ala Tyr Arg Ser Val Asp Glu Val Asn
1               5                   10

<210> SEQ ID NO 57
<211> LENGTH: 13
<212> TYPE: PRT
<213> ORGANISM: Artificial Sequence
<220> FEATURE:
<223> OTHER INFORMATION: PP2AB_297_309

<400> SEQUENCE: 57

Glu Pro His Val Thr Arg Arg Thr Pro Asp Tyr Phe Leu
1               5                   10

<210> SEQ ID NO 58
<211> LENGTH: 13
<212> TYPE: PRT
<213> ORGANISM: Artificial Sequence
<220> FEATURE:
<223> OTHER INFORMATION: PAXI_24_36
```

<400> SEQUENCE: 58

Phe Leu Ser Glu Glu Thr Pro Tyr Ser Tyr Pro Thr Gly
1               5                   10

<210> SEQ ID NO 59
<211> LENGTH: 13
<212> TYPE: PRT
<213> ORGANISM: Artificial Sequence
<220> FEATURE:
<223> OTHER INFORMATION: PDPK1_2_14

<400> SEQUENCE: 59

Ala Arg Thr Thr Ser Gln Leu Tyr Asp Ala Val Pro Ile
1               5                   10

<210> SEQ ID NO 60
<211> LENGTH: 13
<212> TYPE: PRT
<213> ORGANISM: Artificial Sequence
<220> FEATURE:
<223> OTHER INFORMATION: PDPK1_369_381

<400> SEQUENCE: 60

Asp Glu Asp Cys Tyr Gly Asn Tyr Asp Asn Leu Leu Ser
1               5                   10

<210> SEQ ID NO 61
<211> LENGTH: 13
<212> TYPE: PRT
<213> ORGANISM: Artificial Sequence
<220> FEATURE:
<223> OTHER INFORMATION: PECA1_706_718

<400> SEQUENCE: 61

Lys Lys Asp Thr Glu Thr Val Tyr Ser Glu Val Arg Lys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: PGFRB_1002_1014

<400> SEQUENCE: 62

Leu Asp Thr Ser Ser Val Leu Tyr Thr Ala Val Gln Pro
1               5                   10

<210> SEQ ID NO 63
<211> LENGTH: 13
<212> TYPE: PRT
<213> ORGANISM: Artificial Sequence
<220> FEATURE:
<223> OTHER INFORMATION: PGFRB_572_584

<400> SEQUENCE: 63

Val Ser Ser Asp Gly His Glu Tyr Ile Tyr Val Asp Pro
1               5                   10

<210> SEQ ID NO 64
<211> LENGTH: 13
<212> TYPE: PRT
<213> ORGANISM: Artificial Sequence
<220> FEATURE:
<223> OTHER INFORMATION: PGFRB_709_721

<400> SEQUENCE: 64

Arg Pro Pro Ser Ala Glu Leu Tyr Ser Asn Ala Leu Pro
1               5                   10

<210> SEQ ID NO 65
<211> LENGTH: 13
<212> TYPE: PRT
<213> ORGANISM: Artificial Sequence
<220> FEATURE:
<223> OTHER INFORMATION: PGFRB_768_780

<400> SEQUENCE: 65

Ser Ser Asn Tyr Met Ala Pro Tyr Asp Asn Tyr Val Pro
1               5                   10

<210> SEQ ID NO 66
<211> LENGTH: 13
<212> TYPE: PRT
<213> ORGANISM: Artificial Sequence
<220> FEATURE:
<223> OTHER INFORMATION: PGFRB_771_783

<400> SEQUENCE: 66

Tyr Met Ala Pro Tyr Asp Asn Tyr Val Pro Ser Ala Pro
1               5                   10

<210> SEQ ID NO 67
<211> LENGTH: 13
<212> TYPE: PRT
<213> ORGANISM: Artificial Sequence
<220> FEATURE:
<223> OTHER INFORMATION: PRGR_786_798

<400> SEQUENCE: 67

Glu Gln Arg Met Lys Glu Ser Ser Phe Tyr Ser Leu Cys
1               5                   10

<210> SEQ ID NO 68
<211> LENGTH: 13
<212> TYPE: PRT
<213> ORGANISM: Artificial Sequence
<220> FEATURE:
<223> OTHER INFORMATION: PRRX2_202_214

<400> SEQUENCE: 68

Trp Thr Ala Ser Ser Pro Tyr Ser Thr Val Pro Pro Tyr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: PTN11_539_551

<400> SEQUENCE: 69

Ser Lys Arg Lys Gly His Glu Tyr Thr Asn Ile Lys Tyr
1               5                   10

<210> SEQ ID NO 70
<211> LENGTH: 13
<212> TYPE: PRT
<213> ORGANISM: Artificial Sequence
<220> FEATURE:
<223> OTHER INFORMATION: RAF1_332_344

<400> SEQUENCE: 70

```
Pro Arg Gly Gln Arg Asp Ser Ser Tyr Tyr Trp Glu Ile
1               5                   10

<210> SEQ ID NO 71
<211> LENGTH: 13
<212> TYPE: PRT
<213> ORGANISM: Artificial Sequence
<220> FEATURE:
<223> OTHER INFORMATION: RASA1_453_465

<400> SEQUENCE: 71

Thr Val Asp Gly Lys Glu Ile Tyr Asn Thr Ile Arg Arg
1               5                   10

<210> SEQ ID NO 72
<211> LENGTH: 13
<212> TYPE: PRT
<213> ORGANISM: Artificial Sequence
<220> FEATURE:
<223> OTHER INFORMATION: RB_804_816

<400> SEQUENCE: 72

Ile Tyr Ile Ser Pro Leu Lys Ser Pro Tyr Lys Ile Ser
1               5                   10

<210> SEQ ID NO 73
<211> LENGTH: 13
<212> TYPE: PRT
<213> ORGANISM: Artificial Sequence
<220> FEATURE:
<223> OTHER INFORMATION: RBL2_99_111

<400> SEQUENCE: 73

Val Pro Thr Val Ser Lys Gly Thr Val Glu Gly Asn Tyr
1               5                   10

<210> SEQ ID NO 74
<211> LENGTH: 13
<212> TYPE: PRT
<213> ORGANISM: Artificial Sequence
<220> FEATURE:
<223> OTHER INFORMATION: RET_1022_1034

<400> SEQUENCE: 74

Thr Pro Ser Asp Ser Leu Ile Tyr Asp Asp Gly Leu Ser
1               5                   10

<210> SEQ ID NO 75
<211> LENGTH: 13
<212> TYPE: PRT
<213> ORGANISM: Artificial Sequence
<220> FEATURE:
<223> OTHER INFORMATION: RON_1346_1358

<400> SEQUENCE: 75

Ser Ala Leu Leu Gly Asp His Tyr Val Gln Leu Pro Ala
1               5                   10

<210> SEQ ID NO 76
<211> LENGTH: 13
<212> TYPE: PRT
<213> ORGANISM: Artificial Sequence
<220> FEATURE:
<223> OTHER INFORMATION: RON_1353_1365

<400> SEQUENCE: 76
```

Tyr Val Gln Leu Pro Ala Thr Tyr Met Asn Leu Gly Pro
1               5                   10

<210> SEQ ID NO 77
<211> LENGTH: 13
<212> TYPE: PRT
<213> ORGANISM: Artificial Sequence
<220> FEATURE:
<223> OTHER INFORMATION: SRC8_CHICK_470_482

<400> SEQUENCE: 77

Val Ser Gln Arg Glu Ala Glu Tyr Glu Pro Glu Thr Val
1               5                   10

<210> SEQ ID NO 78
<211> LENGTH: 13
<212> TYPE: PRT
<213> ORGANISM: Artificial Sequence
<220> FEATURE:
<223> OTHER INFORMATION: STAT4_714_726

<400> SEQUENCE: 78

Pro Ser Asp Leu Leu Pro Met Ser Pro Ser Val Tyr Ala
1               5                   10

<210> SEQ ID NO 79
<211> LENGTH: 13
<212> TYPE: PRT
<213> ORGANISM: Artificial Sequence
<220> FEATURE:
<223> OTHER INFORMATION: TEC_512_524

<400> SEQUENCE: 79

Arg Tyr Phe Leu Asp Asp Gln Tyr Thr Ser Ser Ser Gly
1               5                   10

<210> SEQ ID NO 80
<211> LENGTH: 13
<212> TYPE: PRT
<213> ORGANISM: Artificial Sequence
<220> FEATURE:
<223> OTHER INFORMATION: TNNT1_2_14

<400> SEQUENCE: 80

Ser Asp Thr Glu Glu Gln Glu Tyr Glu Glu Glu Gln Pro
1               5                   10

<210> SEQ ID NO 81
<211> LENGTH: 13
<212> TYPE: PRT
<213> ORGANISM: Artificial Sequence
<220> FEATURE:
<223> OTHER INFORMATION: TYRO3_679_691

<400> SEQUENCE: 81

Lys Ile Tyr Ser Gly Asp Tyr Tyr Arg Gln Gly Cys Ala
1               5                   10

<210> SEQ ID NO 82
<211> LENGTH: 13
<212> TYPE: PRT
<213> ORGANISM: Artificial Sequence
<220> FEATURE:
<223> OTHER INFORMATION: VGFR1_1040_1052

<400> SEQUENCE: 82

Asp Phe Gly Leu Ala Arg Asp Ile Tyr Lys Asn Pro Asp

```
1               5                10
```

```
<210> SEQ ID NO 83
<211> LENGTH: 13
<212> TYPE: PRT
<213> ORGANISM: Artificial Sequence
<220> FEATURE:
<223> OTHER INFORMATION: VGFR1_1162_1174

<400> SEQUENCE: 83

Val Gln Gln Asp Gly Lys Asp Tyr Ile Pro Ile Asn Ala
1               5                10

<210> SEQ ID NO 84
<211> LENGTH: 13
<212> TYPE: PRT
<213> ORGANISM: Artificial Sequence
<220> FEATURE:
<223> OTHER INFORMATION: VGFR1_1326_1338

<400> SEQUENCE: 84

Asp Tyr Asn Ser Val Val Leu Tyr Ser Thr Pro Pro Ile
1               5                10

<210> SEQ ID NO 85
<211> LENGTH: 13
<212> TYPE: PRT
<213> ORGANISM: Artificial Sequence
<220> FEATURE:
<223> OTHER INFORMATION: VGFR2_1046_1058

<400> SEQUENCE: 85

Asp Phe Gly Leu Ala Arg Asp Ile Tyr Lys Asp Pro Asp
1               5                10

<210> SEQ ID NO 86
<211> LENGTH: 13
<212> TYPE: PRT
<213> ORGANISM: Artificial Sequence
<220> FEATURE:
<223> OTHER INFORMATION: VGFR2_1052_1064

<400> SEQUENCE: 86

Asp Ile Tyr Lys Asp Pro Asp Tyr Val Arg Lys Gly Asp
1               5                10

<210> SEQ ID NO 87
<211> LENGTH: 13
<212> TYPE: PRT
<213> ORGANISM: Artificial Sequence
<220> FEATURE:
<223> OTHER INFORMATION: VGFR2_1168_1180

<400> SEQUENCE: 87

Ala Gln Gln Asp Gly Lys Asp Tyr Ile Val Leu Pro Ile
1               5                10

<210> SEQ ID NO 88
<211> LENGTH: 13
<212> TYPE: PRT
<213> ORGANISM: Artificial Sequence
<220> FEATURE:
<223> OTHER INFORMATION: VGFR2_944_956

<400> SEQUENCE: 88

Arg Phe Arg Gln Gly Lys Asp Tyr Val Gly Ala Ile Pro
1               5                10
```

-continued

```
<210> SEQ ID NO 89
<211> LENGTH: 13
<212> TYPE: PRT
<213> ORGANISM: Artificial Sequence
<220> FEATURE:
<223> OTHER INFORMATION: VGFR2_989_1001

<400> SEQUENCE: 89

Glu Glu Ala Pro Glu Asp Leu Tyr Lys Asp Phe Leu Thr
1               5                   10

<210> SEQ ID NO 90
<211> LENGTH: 13
<212> TYPE: PRT
<213> ORGANISM: Artificial Sequence
<220> FEATURE:
<223> OTHER INFORMATION: VGFR3_1061_1073

<400> SEQUENCE: 90

Asp Ile Tyr Lys Asp Pro Asp Tyr Val Arg Lys Gly Ser
1               5                   10

<210> SEQ ID NO 91
<211> LENGTH: 13
<212> TYPE: PRT
<213> ORGANISM: Artificial Sequence
<220> FEATURE:
<223> OTHER INFORMATION: VINC_815_827

<400> SEQUENCE: 91

Lys Ser Phe Leu Asp Ser Gly Tyr Arg Ile Leu Gly Ala
1               5                   10

<210> SEQ ID NO 92
<211> LENGTH: 13
<212> TYPE: PRT
<213> ORGANISM: Artificial Sequence
<220> FEATURE:
<223> OTHER INFORMATION: ZAP70_485_497

<400> SEQUENCE: 92

Ala Leu Gly Ala Asp Asp Ser Tyr Tyr Thr Ala Arg Ser
1               5                   10

<210> SEQ ID NO 93
<211> LENGTH: 13
<212> TYPE: PRT
<213> ORGANISM: Artificial Sequence
<220> FEATURE:
<223> OTHER INFORMATION: ZBT16_621_633

<400> SEQUENCE: 93

Leu Arg Thr His Asn Gly Ala Ser Pro Tyr Gln Cys Thr
1               5                   10
```

KINASE ACTIVITY SIGNATURES FOR PREDICTING THE RESPONSE OF NON-SMALL-CELL LUNG CARCINOMA PATIENTS TO A PD-1 OR PD-L1 IMMUNE CHECKPOINT INHIBITOR

CROSS-REFERENCE TO RELATED APPLICATIONS

This application is a U.S. national stage entry under 35 U.S.C. § 371 of PCT International Patent Application No. PCT/EP2020/074703, filed Sep. 4, 2020, which claims priority to European Patent Application No. 19195591.3.0, filed Sep. 5, 2019, the contents of each of which are incorporated herein by reference in their entirety.

FIELD OF THE INVENTION

The present invention relates to methods and devices for determining or predicting the response of a patient diagnosed with non-small cell lung carcinoma to specific medicaments. More specifically, the present invention provides methods which measure kinase activity in blood samples of said patients.

BACKGROUND OF THE INVENTION

At present lung cancer is considered to be one of the most important causes of death, especially in adults at the ages from 50 to 69 years old. Long term exposure to smoking is the cause of lung cancer for 90% of the cases. Among male smokers, the lifetime risk of developing lung cancer is about 17%; among female smokers the risk is about 11%.

For non-smokers, the risk of developing lung cancer is about 1%. The main causes for lung cancer in non-smokers are genetic factors, radon gas, asbestos, air pollution and passive smoking. There are two main types of lung cancer: non-small cell lung cancer (NSCLC) (in about 80% of the cases) and small cell lung cancer (in about 17% of the cases). NSCLC can further be classified according to the growth type and spread of the cancer cells. NSCLC can therefore be classified into squamous cell carcinoma, large cell carcinoma and adenocarcinoma. Adenocarcinoma is more frequent in women, Asians and non-smokers. Other less common types of NSCLC are pleomorphic, carcinoid tumor, salivary gland carcinoma, and unclassified carcinoma.

For the diagnosis of NSCLC a lung tissue biopsy is taken. Based on a primary biopsy diagnosis nearby lymph nodes may be biopsied to see if the cancer has spread. Staging of NSCLC is based on the American Joint Committee on Cancer (AJCC) TNM system. The T stands for tumor (how far it has grown within the lung and other factors). The T category is assigned a number (from 0 to 4) based on the tumor's size. N stands for spread to nearby lymph nodes (bean-sized collections of immune system cells, to which cancers often spread first). The N category is assigned a number (from 0 to 3) based on whether the NSCLC cells have spread to lymph nodes or are found in the lymphatic channels connecting the lymph nodes. The M category is based on whether the NSCLC has metastasized (spread) to distant organs, which organs it has reached. It is generally known that most types of lung cancer have a poor prognosis. According to the TNM standards the different stages and survival in the United States are as follows:

Stage IA: The 5-year survival rate is around 49%.
Stage IB: The 5-year survival rate is around 45%.
Stage IIA: The 5-year survival rate is around 30%.

Stage IIB: The 5-year survival rate is around 30%.
Stage IIIA: The 5-year survival rate is around 14%.
Stage IIIB: The 5-year survival rate is around 5%.
Stage IV: The 5-year survival rate is about 1%-2%.

NSCLC treatment options are based on the stage of the disease and may include: surgery, chemotherapy, targeted therapy, immunotherapy and radiation therapy. Early-stage NSCLC can often be cured with surgery alone, but more advanced NSCLC can be much harder to treat because standard cancer treatments such as chemotherapy are not very effective. But in recent years, newer types of immunotherapy and targeted therapies have changed the treatment of this disease, and many new treatments have shown a great deal of promise in treating advanced NSCLC.

The development of molecularly targeted therapy (e.g. small molecules and monoclonal antibodies) has significantly improved outcomes in the metastatic setting for patients with NSCLC whose tumors harbor activated oncogenes such as epidermal growth factor receptor (EGFR) and translocated genes like anaplastic lymphoma kinase (ALK). In addition, immune checkpoint inhibitors have been successfully used to treat NSCLC. This therapy is based upon the fact that T lymphocytes are critical to antitumor immunity, and this antitumor immunity requires activation by an antigen-specific T cell receptor in the context of costimulatory activation. Excess immune activation is being prevented by a naturally occurring feedback mechanism that leads to the expression of negative costimulatory molecules ("checkpoints"). Examples of such checkpoints are cytotoxic T-lymphocyte antigen 4 (CTLA-4), programmed death 1 (PD-1), T cell immunoglobulin 3, and lymphocyte-activation gene 3. Antibodies directed against these checkpoints may restore or augment an antitumor immune response and produce tumor responses in patients with advanced or metastatic NSCLC. Examples of such antibodies are antibodies directed against PD-1 (such as Nivolumab (e.g. Opdivo™), Pembrolizumab (e.g. Keytruda™), or Durvalumab (e.g. Imfinzi™)) or antibodies directed against PD-L1 (such as Atezolizumab (e.g. Tecentriq™), Avelumab (e.g. Bacencio™) and Cemiplimab (e.g. Libtayo™)).

In particular, stage IV NSCLC is very hard to cure, as they have already spread to distant lymph nodes or other areas of the body. While the lung tumors can often be removed by surgery or treated with radiation therapy, metastases in internal organs which cannot be removed may be treated with radiation, immunotherapy, targeted therapy, or chemotherapy. Checkpoint inhibitors can be used alone or in combination. Though, not all patients respond to these therapies. Approximately 20-50% of the patients treated with a checkpoint inhibitor respond to this drug.

Unfortunately, most anti-tumor treatments are associated with undesirable side effects, such as profound nausea, vomiting, or severe fatigue. Also, while anti-tumor treatments have been successful, they do not produce significant clinical responses in all patients who receive them resulting in undesirable side effects, delays, and costs associated with ineffective treatment. Therefore, biomarkers that can be used to predict the response of a subject to an antitumor agent prior to administration thereof are greatly needed.

Given the high incidence of NSCLC and limited efficacy of current treatments, an immuno-oncology therapy prediction NSCLC biomarker and assay for an immuno-oncology therapy prediction NSCLC biomarker is needed.

Also, assays for NSCLC biomarkers as an accurate early indicator for therapeutic response typically require taking a lung tissue biopsy which is considered very unpleasant for the patient.

In view of the above, there remains a pressing need for improved methods that provide a fast and accurate prediction of the response of a patient diagnosed with NSCLC to targeted pharmacotherapy, and immuno-oncology in particular.

SUMMARY OF THE INVENTION

Drug response between individuals differs. Drugs can work more or less efficient; but can also induce adverse drug reactions, toxicity and side effects.

The present invention provides methods and devices that enable the determination of the response of a patient diagnosed with NSCLC to a PD-1 or PD-L1 immune checkpoint inhibitor (ICI) by measuring kinase activity of a sample from said patient.

A first aspect provides a method for determining or predicting the response of a patient diagnosed with non-small-cell lung carcinoma (NSCLC), to a medicament, comprising the steps of:

(a) measuring the kinase activity of at least one kinase of the VEGFR or PDGFR family of kinases;

at least one kinase of the Src family of kinases; and at least one kinase of the Syk family of kinases, in a blood sample obtained from said patient diagnosed with NSCLC thereby providing a kinase activity profile of said blood sample; and (b) determining from said kinase activity profile the response of said patient to said medicament;

wherein said medicament is a PD-1 or PD-L1 immune checkpoint inhibitor; and wherein said blood sample comprises peripheral blood mononuclear cells. In particular embodiments, the at least one kinase of the VEGFR or PDGFR family of kinases is selected from the group consisting of FLT1, FLT3, FLT4, CSF-1R, Kit, PDGFRalpha (i.e. PDGFRα), PDGFRbeta (i.e. PDGFRβ) and KDR; preferably selected from the group consisting of FLT1, FLT3 and FLT4;

the at least one kinase of the Src family of kinases is selected from the group consisting of Src, BLK, LCK, Fyn, YES, Brk, FGR, HCK, Lyn, FRK and Srms; preferably selected from the group consisting of Src, BLK, LCK, Fyn, and YES; and/or the at least one kinase of the Syk family of kinases is selected from the group consisting of Syk and ZAP70.

In particular embodiments, said method further comprises measuring the kinase activity of JAK2, HER4 and/or TRKB.

In particular embodiments, said method comprises measuring the kinase activity of FLT1, FLT3, FLT4, Src, BLK, LCK, Fyn, YES, Syk, ZAP70, JAK2, HER4 and TRKB.

In particular embodiments, said medicament is selected from the group consisting of Nivolumab, Pembrolizumab, Durvalumab, Atezolizumab, Avelumab and Cemiplimab, preferably selected from the group consisting of Nivolumab and Prembrolizumab.

In particular embodiments, step (b) comprises a step (i) of calculating a classifier parameter from said kinase activity profile; and a step (ii) of determining the response of said patient to said medicament on the basis of said classifier parameter.

In particular embodiments, step (b) comprises a step (i) of comparing said kinase activity profile to a first and a second reference kinase activity profile; said first reference kinase activity profile being representative for a good responder to said medicament and said second reference kinase activity profile being representative for a poor responder to said medicament; and a step (ii) of determining response of said patient to said medicament on the basis of the comparison of said kinase activity profile with said first and said second reference kinase activity profile.

In particular embodiments, in step (a) said kinase activity is determined by contacting the sample with at least one protein kinase substrate, thereby providing a phosphorylation profile of said sample, said phosphorylation profile comprising the phosphorylation levels of phosphorylation sites present in all 93 peptide markers as listed in Table 2.

In particular embodiments, said kinase activity profile or said classifier parameter indicates good response, poor response or undetermined response of said patient to said medicament.

In particular embodiments, said non-small-cell lung carcinoma is a stage III or stage IV non-small-cell lung carcinoma.

A further aspect provides the use of the method as taught herein for accessing susceptibility of a patient having non-small-cell lung carcinoma to a medicament, wherein said medicament is a PD-1 or PD-L1 immune checkpoint inhibitor.

A further aspect provides the use of method as taught herein for assessing the pharmaceutical or clinical value of a medicament, wherein said medicament is a PD-1 or PD-L1 immune checkpoint inhibitor.

A further aspect provides a kit for determining the response of a patient diagnosed with non-small-cell lung carcinoma to a medicament, comprising means for measuring the kinase activity of at least one kinase of the VEGFR or PDGFR family of kinases; preferably at least one kinase of the VEGFR or PDGFR family of kinases selected from the group consisting of FLT1, FLT3, FLT4, CSF-1R, Kit, PDG-FRalpha, PDGFRbeta and KDR; more preferably selected from the group consisting of FLT1, FLT3 and FLT4;

at least one kinase of the Src family of kinases; preferably at least one kinase of the Src family of kinases selected from the group of consisting of Src, BLK, LCK, Fyn, YES, Brk, FGR, HCK, Lyn, FRK and Srms; more preferably selected from the group consisting of Src, BLK, LCK, Fyn, and YES; and at least one kinase of the Syk family of kinases, preferably at least one kinase of the Syk family of kinases selected from the group of kinases consisting of Syk and ZAP70, in a blood sample obtained from said patient diagnosed with non-small-cell lung carcinoma (NSCLC); and a computer readable storage medium having recorded thereon one or more programs for carrying out the method of taught herein;

wherein said medicament is a PD-1 or PD-L1 immune checkpoint inhibitor; and wherein said blood sample comprises peripheral blood mononuclear cells.

In particular embodiments, the means for measuring the kinase activity of at least one kinase of the VEGFR or PDGFR family of kinases;

at least one kinase of the Src family of kinases; and at least one kinase of the Syk family of kinases;

is at least one array comprising all of the 93 peptide markers as listed in Table 2.

A further aspect provides a computer program product for use in conjunction with a computer having a processor and a memory connected to the processor, said computer program product comprising a computer readable storage medium having a computer program mechanism encoded thereon, wherein said computer program mechanism is loaded into the memory of said computer and causes said computer to carry out the method as taught herein.

These and further aspects and embodiments are described in the following sections and in the claims.

DETAILED DESCRIPTION OF THE INVENTION

Figure 1:
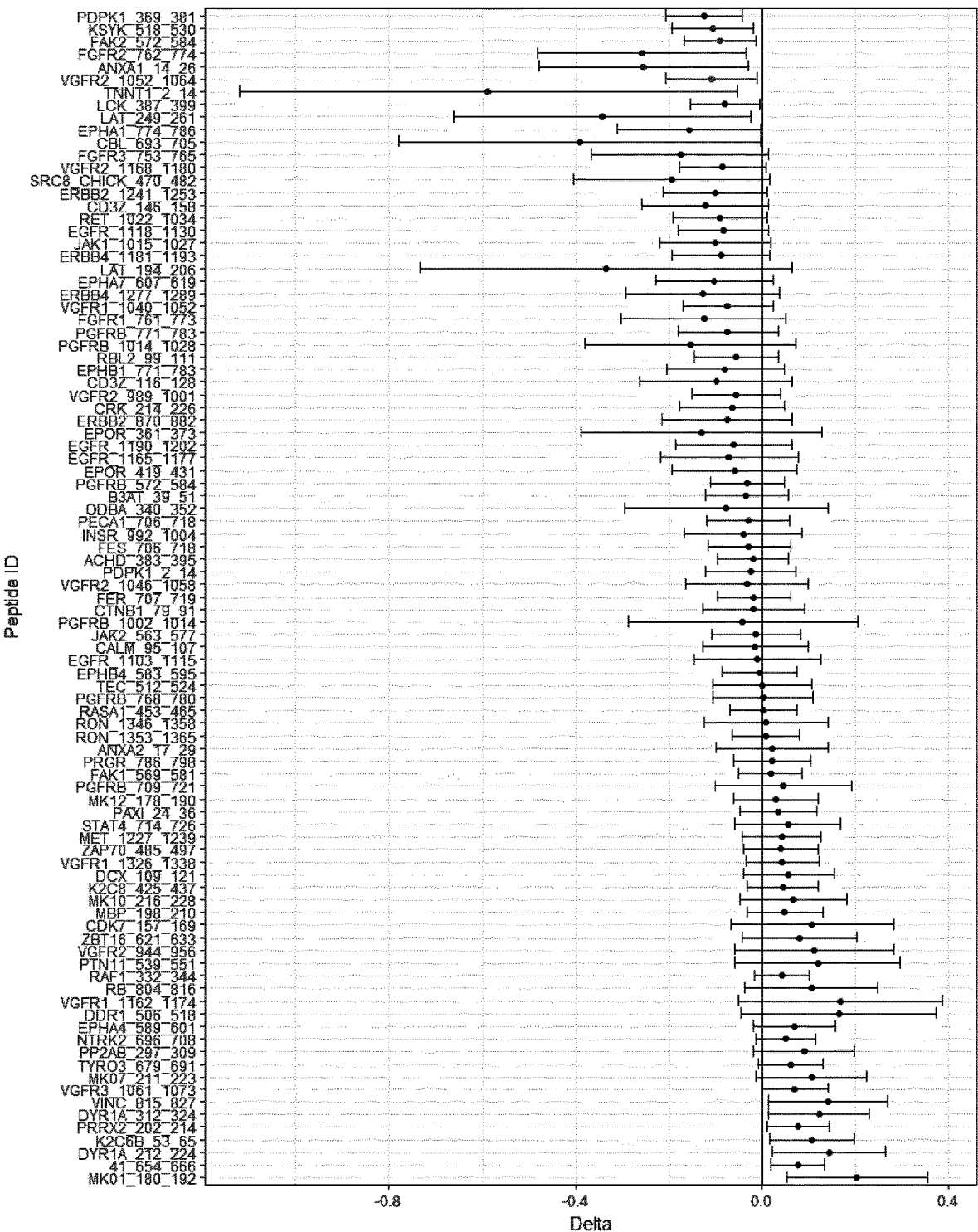
FIG. 1. Differential kinase activity profile between patients with early progression and patients with late/no progression on treatment with anti-PD1 immune checkpoint inhibitor (ICI). The figure shows for each peptide the difference Delta between the early progression and the late/no progression group. The error bars indicate the 95% confidence interval for this difference. Delta>0 indicates a higher phosphorylation of the substrate in the late/no progression group and Delta<0 indicates a higher phosphorylation of the substrate in early progression group. The name of the peptide markers ("peptide ID") refers to the associated proteins and to the start and the end position of the amino acid sequence.

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +1-0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods and devices that enable the determination of the response of a patient diagnosed with NSCLC to a medicament, more particularly to a PD-1 or PD-L1 immune checkpoint inhibitor, by measuring kinase activity of a blood sample, obtained from said patient diagnosed with NSCLC. The present invention further shows how the method and devices can be used to predict the response and/or resistance, especially the response, of patients diagnosed with NSCLC to a medicament, more particularly to a PD-1 or PD-L1 immune checkpoint inhibitor. The method of the present invention therefore adds to the existing assays currently used to select therapies in NSCLC patients.

The method according to the present invention can be used to predict or assess both primary and secondary resistance to a medicament, more particularly to a PD-1 or PD-L1 immune checkpoint inhibitor. With primary resistance is meant resistance in NSCLC patients that never respond to a medicament, more particularly to a PD-1 or PD-L1 immune checkpoint inhibitor. In secondary resistance is meant resistance in NSCLC patients which first respond to a medicament, more particularly to a PD-1 or PD-L1 immune checkpoint inhibitor, but after a few months or years, resistance occurs.

For purposes of the present invention, and as used herein the term "kinase activity" or "protein kinase activity" refer to the formation of reaction product(s) by a certain amount of kinase or protein kinase acting on a substrate during the course of the assay.

Protein kinase activity is referred to as the activity of protein kinases. A protein kinase is a generic name for all enzymes that transfer a phosphate to a protein. About two percent of the human genome contains transcription information for the formation of protein kinases. Currently, there are about 518 known different protein kinases. However, because three to four percent of the human genome is a code for the formation of protein kinases, there may be many more separate kinases in the human body.

A protein kinase is a kinase enzyme that modifies other proteins by covalently coupling phosphate groups to them. This process or activity is also referred to as phosphorylation. Phosphorylation can therefore be regarded as the process of the addition of a phosphate group to a substrate. Phosphorylation usually results in a functional change of the substrate by changing kinase activity, cellular location, or association with other proteins. Up to 30 percent of all proteins may be modified by kinase activity, and kinases are known to regulate the majority of cellular pathways, especially those involved in signal transduction, the transmission of signals within the cell. The chemical activity of a kinase involves removing a phosphate group from ATP or GTP and covalently attaching it to amino acids such as serine, threonine, tyrosine, histidine, aspartic acid and/or glutamic acid that have a free hydroxyl group. Most known kinases act on both serine and threonine, others act on tyrosine, and a number act on all serine, threonine and tyrosine.

The protein kinase activity monitored with the method of the present invention is preferably directed to protein kinases acting towards serine, threonine and/or tyrosine, preferably acting on both serine and threonine, on tyrosine or on serine, threonine and tyrosine and more preferably the method of the present invention if preferably directed to protein kinases acting towards tyrosine.

Protein kinases are distinguished by their ability to phosphorylate substrates on discrete sequences. These sequences have been determined by sequencing the amino acids around the phosphorylation sites and are usually distinct for each protein kinase. The recognition sequence on each substrate is specific for each kinase catalyst.

Because protein kinases have profound effects on a cell, their activity is highly regulated. Kinases are turned on or off by for instance phosphorylation, by binding of activator proteins or inhibitor proteins, or small molecules, or by controlling their location in the cell relative to their substrates. Deregulated activity is a frequent cause of disease, particularly cancer, where kinases regulate many aspects that control cell growth, movement and death. Kinases also play an important role in the activation of cells of the immune system (for example see Weiss A., Kinases and phosphatases of the immune system, Immunological Reviews 2009, Vol. 228: 5-8). Therefore, monitoring the protein kinase activity in tissues can be of great importance and a large amount of information can be obtained when comparing the kinase activity of different tissue samples.

As described in the present invention, the inventors have surprisingly found that the response of a patient diagnosed with NSCLC to a medicament, more particularly to a PD-1 or PD-L1 immune checkpoint inhibitor, can be predicted and/or determined on the basis of the measurement of the kinase activity, preferably protein kinase activity, of a blood sample taken from said patient diagnosed with NSCLC. The methods according to present invention enable to provide information regarding the efficacy of the targeted pharmacotherapy treatment, and more specifically provide an early determination of the most suited treatment of the NSCLC patient. Preferably, the measurement of the kinase activity is performed by contacting the blood sample from a patient diagnosed NSCLC with one or more kinase substrates, preferably protein kinase substrates, thereby generating one or more phosphorylation profile(s). Said protein kinase substrates as used herein, are preferably peptides, proteins or peptide mimetics. The protein kinase substrates each comprise, preferably one or more, phosphorylation sites that can be phosphorylated by the protein kinases present in the sample. Therefore, exposure of a protein kinase substrate to a sample comprising a protein kinase results in the phosphorylation of one or more of the phosphorylation sites of the protein kinase substrate. This phosphorylation activity can be measured using techniques known in the art. Therefore, in particular embodiments, during the measurement method the kinase enzymes present in the sample will phosphorylate, preferably one or more, of the phosphorylation sites on one or more protein kinase substrate.

Present inventors have observed essential differences between kinase activity of NSCLC tumors having a different response to a medicament, more particularly to a PD-1 or PD-L1 immune checkpoint inhibitor. More particularly, present inventors have surprisingly found that the aberrant activity of at least one kinase of the VEGFR or PDGFR family of kinases, preferably selected from the group consisting of FLT1, FLT3 and FLT4;

at least one kinase of the Src family of kinases, preferably selected from the group consisting of Src, BLK, LCK, Fyn, and YES;

at least one kinase of the Syk family of kinases, preferably selected from the group consisting of Syk; and optionally at least one kinase selected from the group consisting of JAK2, HER4, and TRKB, may especially be used for predicting the response of a patient diagnosed with NSCLC, to a medicament, more particularly to a PD-1 or PD-L1 immune checkpoint inhibitor.

For example, at least one kinase of the VEGFR or PDGFR family of kinases, preferably selected from the group consisting of FLT1, FLT3 and FLT4;

at least one kinase of the Src family of kinases, preferably selected from the group consisting of Src, BLK, LCK, Fyn, and YES; and at least one kinase of the Syk family of kinases, preferably selected from the group consisting of Syk and ZAP70.

present in a blood sample from patients suffering from NSCLC will phosphorylate protein kinase substrates differently depending on the response to the medicament with which the patient is envisaged to be treated or is being treated. Accordingly, phosphorylation signals differ between the blood samples, resulting in phosphorylation patterns that differ depending on response to the medicament.

For purposes of the present invention, and as used herein the term "pharmacotherapy", or "pharmacotherapeutics" or "drug treatment" refers to the use of a pharmaceutical drug, also referred to as medicine or medicament wherein said pharmacotherapy is intended for use in the diagnosis, cure, mitigation, treatment, or prevention of disease.

The kinase activity of at least one kinase of the VEGFR or PDGFR family of kinases, preferably selected from the group consisting of FLT1, FLT3 and FLT4;

at least one kinase of the Src family of kinases, preferably selected from the group consisting of Src, BLK, LCK, Fyn, and YES; and at least one kinase of the Syk family of kinases, preferably selected from the group consisting of Syk and ZAP70 in a blood sample obtained from a patient diagnosed with NSCLC could serve as an accurate early indicator for therapeutic response in a subject to measure the effectiveness of candidate NSCLC inhibitory agents, more particularly PD-1 or PD-L1 immune checkpoint inhibitors.

Accordingly, a first aspect provides in a method for predicting the response of a patient diagnosed with NSCLC, to a medicament, comprising the steps of:

(a) measuring the kinase activity of at least one kinase of the vascular endothelial growth factor receptor (VEGFR) or platelet-derived growth factor receptor (PDGFR) family of kinases;

at least one kinase of the Src family of kinases; and at least one kinase of the Spleen tyrosine kinase (Syk) family of kinases, in a blood sample obtained from said patient diagnosed with NSCLC thereby providing a kinase activity profile of said blood sample; and (b) determining from said kinase activity profile the response of said patient to said medicament;

wherein said medicament is a PD-1 or PD-L1 immune checkpoint inhibitor; and wherein said blood sample comprises peripheral blood mononuclear cells.

In other words, provided herein is a method for predicting sensitivity (which may also be denoted as responsiveness or susceptibility) or resistance (which may also be denoted as unresponsiveness or insusceptibility) of a patient diagnosed with NSCLC, to a medicament, comprising the steps of:

(a) measuring the kinase activity of at least one kinase of the vascular endothelial growth factor receptor (VEGFR) or platelet-derived growth factor receptor (PDGFR) family of kinases;

at least one kinase of the Src family of kinases; and at least one kinase of the Spleen tyrosine kinase (Syk) family of kinases, in a blood sample obtained from said patient diagnosed with NSCLC thereby providing a kinase activity profile of said blood sample; and (b) determining from said kinase activity profile the sensitivity or resistance of said patient to said medicament;

wherein said medicament is a PD-1 or PD-L1 immune checkpoint inhibitor; and wherein said blood sample comprises peripheral blood mononuclear cells.

In certain embodiments, the methods or uses as taught herein are useful for predicting an outcome of treatment with a PD-1 or PD-L1 ICI in a patient diagnosed with NSCLC.

The phrases "determining the response" and "predicting the response" may be used interchangeably herein.

The terms "predicting", "prediction" or "predictive" as used herein have their generally accepted meaning and preferably refer to an advance declaration, indication or foretelling of a response or reaction to a therapy in a patient, preferably wherein said patient has not (yet) been treated with the therapy. For example, a prediction of sensitivity (or responsiveness or susceptibility) to treatment with a medicament in a patient may indicate that the subject will respond or react to the treatment, for example within a certain time period, e.g., so that the patient will have a clinical benefit (e.g., will display reduced tumour load, or will display complete or partial response, will display stable disease for a period of at least 90 days, will display late (after 140 days) or no disease progression) from the treatment. A prediction of insensitivity (or unresponsiveness or insusceptibility or resistance) to treatment with a medicament in a patient diagnosed with NSCLC may indicate that the patient will minimally or not respond or react to the treatment, for example within a certain time period, e.g., so that the patient will have no clinical benefit (e.g., will not display a therapeutically meaningful reduction in tumour load, will display disease progression, will display early (within 140 days) disease progression) from the treatment.

In certain embodiments, the response of said patient diagnosed with NSCLC to said medicament is the time to progression of disease upon treatment with said medicament, wherein a good responder has a late (e.g. more than 140 days after treatment with said medicament) or no progression of disease upon treatment with said medicament and the poor responder has an early progression (e.g. less than 140 days after treatment with said medicament) of disease upon treatment with said medicament.

The terms "sensitivity", "responsiveness" or "susceptibility" may be used interchangeably herein, have their generally accepted meaning and preferably refer to the quality that predisposes a patient diagnosed with NSCLC to be sensitive or reactive to treatment with a PD-1 or PD-L1 ICI. Preferably, a patient is "sensitive", "responsive" or "susceptible" (which terms may be used interchangeably) to treatment with a PD-1 or PD-L1 ICI if the subject will have a clinical benefit from the treatment. Preferably, a neoplastic tissue, such as a tumour, is "sensitive", "responsive", or "susceptible" to treatment with an antineoplastic agent if the proliferation rate of the neoplastic tissue is inhibited as a result of contact with a therapeutically effective amount of the PD-1 or PD-L1 ICI, compared to the proliferation rate of the neoplastic tissue in the absence of contact with the PD-1 or PD-L1 ICI.

The terms "insensitivity", "unresponsiveness", "insusceptibility" or "resistance" may be used interchangeably herein, have their generally accepted meaning and preferably refer to the quality that predisposes a patient diagnosed with NSCLC to a minimal (e.g. clinically insignificant) or no response to treatment with a PD-1 or PD-L1 ICI. Preferably, a patient is "insensitive", "unresponsive", "unsusceptible" or "resistant" (which terms may be used interchangeably) to treatment with a PD-1 or PD-L1 ICI if the patient will have no clinical benefit from the treatment. Preferably, a neoplastic tissue, including a tumour, is "insensitive", "unresponsive", "unsusceptible" or "resistant" to treatment with a PD-1 or PD-L1 ICI if the proliferation rate of the neoplastic tissue is not inhibited, or inhibited to a very low (e.g. therapeutically insignificant) degree, as a result of contact with the PD-1 or PD-L1 ICI, compared to the proliferation rate of the neoplastic tissue in the absence of contact with the PD-1 or PD-L1 ICI.

The methods as disclosed herein may allow making a prediction that a patient diagnosed with NSCLC will be responsive to treatment with a PD-1 or PD-L1 ICI or will be non-responsive to treatment with a PD-1 or PD-L1 ICI. This may in certain embodiments include predicting that a patient with NSCLC will have a comparatively low probability (e.g., less than 50%, less than 40%, less than 30%, less than 20% or less than 10%) of being responsive to treatment with a PD-1 or PD-L1 ICI; or that a patient with NSCLC will have a comparatively high probability (e.g., at least 50%, at least 60%, at least 70%, at least 80% or at least 90%) of being responsive (or of being a responder) to treatment with a PD-1 or PD-L1 ICI.

The present methods of evaluating kinase activity to provide information as to the patient's responsiveness to a PD-1 or PD-L1 ICI are generally performed in vitro, on a blood sample obtained from a patient. The term "in vitro" has its generally accepted meaning and preferably denotes outside, or external to, animal or human body. The term "ex vivo" has its generally accepted meaning and preferably refers to tissues or cells removed from an animal or human body and maintained or propagated outside the body, e.g., in a culture vessel. Preferably, the term "in vitro" as used herein should be understood to include "ex vivo". The term "in vivo" has its generally accepted meaning and preferably denotes inside, on, or internal to, animal or human body.

The term "VEGFR family of kinases" as used herein refers to a family of transmembrane proteins, namely receptor tyrosine kinases, which transduce signals from the extracellular environment to the cytoplasm and nucleus.

The term "PDGFR family of kinases" as used herein refers to a family of transmembrane proteins, namely receptor tyrosine kinases, which transduce signals from the extracellular environment to the cytoplasm and nucleus.

The term "Src family of kinases" as used herein refers to a family proteins, namely non-receptor tyrosine kinases, which transduce signals in the cytoplasm.

The term "Syk family of kinases" as used herein refers to a family of proteins, namely non-receptor tyrosine kinases, which transduce signals in the cytoplasm.

Exemplary human (Homo sapiens) members of kinase of the VEGFR or PDGFR family of kinases include:

Fms-like tyrosine kinase 1 (FLT1) with UniprotID P17948 (i.e. VEGFR family),

Fms-like tyrosine kinase 3 (FLT3) with UniprotID P36888 (i.e. PDGFR family),

Fms-like tyrosine kinase 4 (FLT4) with UniprotID P35916 (i.e. VEGFR family), macrophage colony-stimulating factor 1 receptor (CSF-1R) with UniprotID P07333 (i.e. PDGFR family), Mast/stem cell growth factor receptor Kit (Kit) with UniprotID P10721 (i.e. PDGFR family), Platelet-derived growth factor receptor alpha (PDGFRalpha) with UniprotID P16234 (i.e. PDGFR family), Platelet-derived growth factor receptor beta (PDGFRbeta) with UniprotID P09619 (i.e. PDGFR family), and Kinase insert domain receptor (KDR) with UniprotID P35968 (i.e. VEGFR family).

Furthermore, exemplary human (Homo sapiens) members of kinase of the Src family of kinases include:

proto-oncogene tyrosine-protein kinase Src (Src), with UniprotID P12931,

B lymphocyte kinase (BLK) with UniprotID P51451,

Leukocyte C-terminal Src kinase (LCK) with UniprotID P06239,

Proto-oncogene c-Fyn (Fyn) with UniprotID P06241,

Tyrosine-protein kinase Yes (YES) with UniprotID P07947,

Breast tumor kinase (Brk) with UniprotID Q13882,

FGR with UniprotID P09769,

Hematopoietic cell kinase (HCK) with UniprotID P08631,

Lyn with UniprotID P07948,

FYN-related kinase (FRK) with UniprotID P42685, and

Srms with UniprotID Q9H3Y6.

Furthermore, exemplary human (Homo sapiens) members of kinase of the Syk family of kinases include:

Spleen tyrosine kinase (Syk) with UniprotID P43405, and 70 kDa zeta-chain associated protein (ZAP70) with UniprotID P43403.

In particular embodiments, the at least one kinase of the VEGFR or PDGFR family of kinases is selected from the group consisting of Fms-like tyrosine kinase 1 (FLT1), Fms-like tyrosine kinase 3 (FLT3), Fms-like tyrosine kinase 4 (FLT4), macrophage colony-stimulating factor 1 receptor (CSF-1R), Mast/stem cell growth factor receptor Kit (Kit), Platelet-derived growth factor receptor alpha (PDGFRalpha), Platelet-derived growth factor receptor beta (PDGFRbeta) and Kinase insert domain receptor (KDR); preferably the at least one kinase of the VEGFR or PDGFR family of kinases is selected from the group consisting of consisting of FLT1, FLT3, and FLT4;

the at least one kinase of the Src family of kinases is selected from the group consisting of proto-oncogene tyrosine-protein kinase Src (Src), B lymphocyte kinase (BLK), Leukocyte C-terminal Src kinase (LCK), Proto-oncogene c-Fyn (Fyn), Tyrosine-protein kinase Yes (YES), Breast tumor kinase (Brk), FGR, Hematopoietic cell kinase (HCK) Lyn, FYN-related kinase (FRK) and Srms; preferably the at least one kinase of the Src family of kinases is selected from the group consisting of consisting of Src, BLK, LCK, Fyn and YES, and/or the at least one kinase of the Syk family of kinases is selected from the group consisting of Spleen tyrosine kinase (Syk) and 70 kDa zeta-chain associated protein (ZAP70).

In particular embodiments, the method for predicting the response of a patient diagnosed with NSCLC, to a medicament, comprises measuring the kinase activity of at least two, at least three, at least four, at least five, at least six, at least seven or at least eight kinases of the VEGFR or PDGFR family of kinases; preferably at least two, at least three, at least four, at least five, at least six, at least seven or all eight kinases of the VEGFR or PDGFR family of kinases selected from the group consisting of FLT1, FLT3, FLT4, CSF-1R, Kit, PDGFRalpha, PDGFRbeta and KDR; more preferably at least two, preferably all three, kinases of the VEGFR or PDGFR family of kinases selected from the group consisting of FLT1, FLT3 and FLT4;

at least two, at least three, at least four, at least five, at least six, at least seven, at least eight, at least nine, at least ten, or at least eleven kinases of the Src family of kinases; preferably at least two, at least three, at least four, at least five, at least six, at least seven, at least eight, at least nine, at least ten, or all eleven kinases of the Src family of kinases selected from the group consisting of Src, BLK, LCK, Fyn, YES, Brk, FGR, HCK, Lyn, FRK and Srms; more preferably at least two, at least three, at least four or all five kinases of the Src family of kinases selected from the group consisting of Src, BLK, LCK, Fyn, and YES; and at least one or at least two kinases of the Syk family of kinases, preferably two kinases of the Syk family of kinases selected from the group consisting of Syk and ZAP70, in a blood sample obtained from said patient diagnosed with NSCLC.

In more particular embodiments, the method for predicting the response of a patient diagnosed with NSCLC, to a medicament, comprises measuring the kinase activity of FLT1, FLT3, FLT4, Src, BLK, LCK, Fyn, YES, Syk, and ZAP70 in a blood sample obtained from said patient diagnosed with NSCLC.

In particular embodiments, the method for predicting the response of a patient diagnosed with NSCLC, to a medicament, further comprises measuring the kinase activity of Janus kinase 2 (JAK2), Tyrosine kinase-type cell surface receptor HER4 (HER4) and/or Tropomyosin-related kinase B (TRKB) in a blood sample obtained from said patient diagnosed with NSCLC.

In particular embodiments, the method for predicting the response of a patient diagnosed with NSCLC, to a medicament, comprises measuring the kinase activity of FLT1, FLT3, FLT4, Src, BLK, LCK, Fyn, YES, Syk, ZAP70, JAK2, HER4 and TRKB, as listed in Table 1, in a blood sample obtained from said patient diagnosed with NSCLC.

In particular embodiments, the method for predicting the response of a patient diagnosed with NSCLC, to a medicament, comprises measuring at least 3, at least 4, at least 5, at least 6, at least 7, at least 8, at least 9, at least 10, at least 11, or at least 12, preferably all 13 of the kinases, as listed in Table 1.

TABLE 1 list of 13 kinases used for predicting the response of a patient diagnosed with NSCLC to a PD-1 or PD-1L immune checkpoint inhibitor.

| Kinase |
| --- |
| FLT1 |
| FLT3 |
| FLT4 |
| JAK2 |
| HER4 |
| TRKB |
| Src |
| BLK |
| LCK |
| Fyn |
| YES |
| Syk |
| ZAP70 |

Exemplary human (Homo sapiens) members of the kinases as listed in Table 1 include:
  Fms-like tyrosine kinase 1 (FLT1) with UniprotID P17948,
  Fms-like tyrosine kinase 3 (FLT3) with UniprotID P36888,
  Fms-like tyrosine kinase 4 (FLT4) with UniprotID P35916,
  Janus kinase 2 (JAK2) with UniprotID 060674,
  Tyrosine kinase-type cell surface receptor HER4 (HER4) with UniprotID Q15303,
  Tropomyosin-related kinase B (TRKB) with UniprotID Q16620,
  proto-oncogene tyrosine-protein kinase Src (Src), with UniprotID P12931,
  B lymphocyte kinase (BLK) with UniprotID P51451,
  Leukocyte C-terminal Src kinase (LCK) with UniprotID P06239,
  Proto-oncogene c-Fyn (Fyn) with UniprotID P06241,
  Tyrosine-protein kinase Yes (YES) with UniprotID P07947,
  Spleen tyrosine kinase (Syk) with UniprotID P43405, and
  70 kDa zeta-chain associated protein (ZAP70) with UniprotID P43403

The reference to any marker, including any kinase, peptide, polypeptide, protein, or nucleic acid, corresponds to the marker, kinase, peptide, polypeptide, protein, nucleic acid, commonly known under the respective designations in the art. The terms encompass such markers, kinases, peptides, polypeptides, proteins, or nucleic acids of any organism where found, and particularly of animals, preferably warm-blooded animals, more preferably vertebrates, yet more preferably mammals, including humans and non-human mammals, still more preferably of humans. The terms particularly encompass such markers, kinases, peptides, polypeptides, proteins, or nucleic acids with a native sequence, i.e., ones of which the primary sequence is the same as that of the markers, kinases, peptides, polypeptides, proteins, or nucleic acids found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to post-transcriptional or post-translational modifications. Any such variants or isoforms of markers, kinases, peptides, polypeptides, proteins, or nucleic acids are intended herein. Accordingly, all sequences of markers, kinases, peptides, polypeptides, proteins, or nucleic acids found in or derived from nature are considered "native". The terms encompass the markers, kinases, peptides, polypeptides, proteins, or nucleic acids when forming a part of a living organism, organ, tissue or cell, when forming a part of a biological sample, as well as when at least partly isolated from such sources.

In particular embodiments, the method for predicting the response of a patient diagnosed with NSCLC, to a medicament, further comprises measuring the kinase activity of at least one member of the TAM family of RTKs, preferably at least one of the group of TAM family members of RTKs consisting of MER proto-oncogene, tyrosine kinase (MERTK), TYRO3 protein tyrosine kinase (TYRO3) and AXL receptor tyrosine kinase (AXL), in a blood sample obtained from said patient diagnosed with NSCLC.

In particular embodiments, the method comprises measuring the kinase activity of
  at least one kinase of the VEGFR or PDGFR family of kinases selected from the group consisting of FLT1, FLT3 and FLT4;
  at least one kinase of the Src family of kinases selected from the group consisting of Src, BLK, LCK, Fyn, and YES;
  at least one kinase of the Syk family of kinases selected from the group consisting of Syk and ZAP70; and
  at least one member of the TAM family of RTKs, preferably at least one member of the TAM family of RTKs selected from the group consisting of MERTK, TYRO3 and AXL.

In particular embodiments, the method comprises measuring the kinase activity of
  at least one kinase of the VEGFR or PDGFR family of kinases, preferably at least one kinase of the VEGFR or PDGFR family of kinases selected from the group consisting of FLT1, FLT3 and FLT4;
  at least one kinase of the Src family of kinases, preferably at least one kinase of the Src family of kinases selected from the group consisting of Src, BLK, LCK, Fyn, and YES;
  at least one kinase of the Syk family of kinases, preferably at least one kinase of the Syk family of kinases selected from the group consisting of Syk and ZAP70;
  at least one kinase selected from the group consisting of JAK2, HER4 and TRKB; and
  at least one member of the TAM family of RTKs, preferably at least one member of the TAM family of RTKs selected from the group consisting of MERTK, TYRO3 and AXL,
in a blood sample obtained from said patient diagnosed with NSCLC.

The term "TAM family of receptor tyrosine kinases" as used herein refers to a family of transmembrane proteins, namely receptor tyrosine kinases, which transduce signals from the extracellular environment to the cytoplasm and nucleus. The TAM family of RTKs is distinguished from other RTK families by a conserved amino acid sequence, KW (I/L)A(I/L)ES, within the kinase domain (cytosolic region). Also the adhesion molecule-like domains in the extracellular region have conserved sequences. Non-limiting examples of members of the TAM family of RTKs include MERTK, TYRO-3 and AXL, which is also known as UFO.

Exemplary human (Homo sapiens) members of the TAM family of RTKs include

AXL receptor tyrosine kinase with Swissprot entry or UniProtID P30530;

MER proto-oncogene, tyrosine kinase with Swissprot entry or UniProtID Q12866; and TYRO3 protein tyrosine kinase with Swissprot entry or UniProtID: Q06418.

The skilled person will understand that when the number of kinases of which the activity is determined according to the method as taught herein increases, so will increase the specificity, accuracy and sensitivity of the method according to the present invention. The highest method accuracy will be obtained when the kinase activity of all kinases as listed in Table 1, optionally in combination with at least one member of the TAM family of RTKs selected from the group consisting of MERTK, TYRO3 and AXL, is used.

The person skilled in the art will understand that the determination of the kinase activity of:

at least one kinase of the VEGFR or PDGFR family of kinases, preferably at least one kinase of the VEGFR or PDGFR family of kinases selected from the group consisting of FLT1, FLT3 and FLT4;

at least one kinase of the Src family of kinases, preferably at least one kinase of the Src family of kinases selected from the group consisting of Src, BLK, LCK, Fyn, and YES;

at least one kinase of the Syk family of kinases, preferably at least one kinase of the Syk family of kinases selected from the group consisting of Syk and ZAP70;

optionally at least one kinase selected from the group consisting of JAK2, HER4 and TRKB; and optionally at least one member of the TAM family of RTKs, preferably at least one member of the TAM family of RTKs selected from the group consisting of MERTK, TYRO3 and AXL, provides a kinase activity profile or a kinase activity signature of said sample.

As used in the present invention, the term "kinase activity profile" or "kinase activity signature" refers to a data set representative for the kinase activity (presence, absence and/or quantity, preferably quantity) of, preferably one or more, kinases present in the sample. A kinase activity profile can also be generated when determining the activity of the kinases as taught herein in different test conditions such as for example by comparing the kinase activity of a sample in the presence and absence of a kinase activity modulating compound or medicament (e.g. a kinase inhibitor). More frequently kinase activity profiles of a sample will be measured by determining the kinase activity of all kinases as taught herein in the same experiment, or in sequentially carried out experiments.

As referred to in the present application NSCLC regards one of the main types of lung cancer and accounts for about 85% of all lung cancers. NSCLC can be further divided into three subtypes, namely squamous cell carcinoma, large cell carcinoma and adenocarcinoma. Adenocarcinoma is the most common type and starts in the mucus making gland cells in the lining of the airways, squamous cell cancer develops in the flat cells that cover the surface of the airways and grows near the centre of the lung and large cell carcinoma appear large and round under the microscope. Other less common types of NSCLC are pleomorphic, carcinoid tumor, salivary gland carcinoma, and unclassified carcinoma.

As used in the present invention, the term "sample" refers to a sample obtained from an organism (patient) such as human or from components (e.g. tissue or cells) of such an organism. Blood is considered a specialized form of connective tissue. Therefore, the sample can be a blood sample. Lung tissue biopsies are considered unpleasant for the patient. Therefore, other samples than NSCLC tumor tissue samples, such as blood samples, are preferred.

In particular embodiments, said sample is derived from peripheral blood, or immune cells isolated or enriched from peripheral blood (e.g. peripheral blood mononuclear cells, PBMCs). In more particular embodiments, said sample is a blood sample obtained from said patient comprising peripheral blood monocytes (PBMCs). Said sample is preferably a fresh or a fresh frozen sample. More preferably, said sample refers to a lysate of blood-derived PBMCs, which are preferably isolated by Ficoll-Isopaque density centrifugation or by any methods known in the art.

In a preferred embodiment of the present invention said sample is a sample that has undergone a preparation step prior to the steps according to the method of the present invention. Preferably said preparation step is a step where the protein kinases present in said sample are released from the tissue by lysis. Additionally the kinases in the sample may be stabilized, maintained, enriched or isolated, and the measurement of the kinase activity as performed in step (a) occurs on the enriched or isolated protein kinase sample. By first enriching protein kinases in the sample or isolating protein kinases from the sample the subsequent measurement of the kinase activity will occur in a more efficient and reliable manner. Also the clarity and intensity of the obtained phosphorylation signal will be increased as certain contaminants are being removed during the enriching or isolating step.

In particular embodiments, said sample is obtained from a patient diagnosed with NSCLC and refractory to a first line therapy (e.g. platinum-based therapy).

In particular embodiments, said sample is obtained from a patient diagnosed with NSCLC before onset of treatment with a second line therapy (e.g. PD-1 immune checkpoint inhibitors or PD-L1 immune checkpoint inhibitors, and/or a combination thereof and/or analogs thereof, preferably Nivolumab).

In particular embodiments, step (b) of the method for predicting the response of a patient diagnosed with NSCLC to a medicament as taught herein (i.e. the step of determining from said kinase activity profile the response of said patient to said medicament) comprises a step (i.1) of comparing said kinase activity profile to a first and a second reference kinase activity profile; said first reference kinase activity profile being representative for a good responder to said medicament and said second reference kinase activity profile being representative for a poor responder to said medicament; and a step (ii.1) of determining response of said patient to said medicament on the basis of the comparison of said kinase activity profile with said first and said second reference kinase activity profile.

Accordingly, in a particular embodiment, the present invention relates to a method for predicting the response of a patient diagnosed with NSCLC cancer, to a medicament, comprising the steps of:

(a) measuring the kinase activity of
  at least one kinase of the VEGFR or PDGFR family of
    kinases, preferably at least one kinase of the VEGFR
    or PDGFR family of kinases selected from the group
    consisting of FLT1, FLT3 and FLT4;
  at least one kinase of the Src family of kinases, pref-
    erably at least one kinase of the Src family of kinases
    selected from the group consisting of Src, BLK,
    LCK, Fyn, and YES; and
  at least one kinase of the Syk family of kinases,
    preferably at least one kinase of the Syk family of
    kinases selected from the group consisting of Syk
    and ZAP70, in a blood sample obtained from said
    patient diagnosed with NSCLC thereby providing a
    kinase activity profile of said blood sample;
  (i.1) comparing said kinase activity profile to a first and a
    second reference kinase activity profile; said first ref-
    erence kinase activity profile being representative for a
    good responder to said medicament and said second
    reference kinase activity profile being representative
    for a poor responder to said medicament; and
  (ii.1) determining the response of said patient to said
    medicament on the basis of the comparison of said
    kinase activity profile with said first and said second
    reference kinase activity profile.
In further particular embodiments, the method for pre-
dicting the response of a patient diagnosed with NSCLC to
a medicament as taught herein comprises the step of
  (a) measuring the kinase activity (i.e. absence, presence
and/or level, preferably level) of of said
  at least one kinase of the VEGFR or PDGFR family of
    kinases, preferably at least one kinase of the VEGFR or
    PDGFR family of kinases selected from the group
    consisting of FLT1, FLT3 and FLT4;
  at least one kinase of the Src family of kinases, preferably
    at least one kinase of the Src family of kinases selected
    from the group consisting of Src, BLK, LCK, Fyn, and
    YES; and
  at least one kinase of the Syk family of kinases, preferably
    at least one kinase of the Syk family of kinases selected
    from the group consisting of Syk and ZAP70,
in a blood sample obtained from said patient diagnosed with
NSCLC thereby providing a kinase activity profile of said
blood sample;
  (i.2) comparing said kinase activity profile to a reference
kinase activity profile, said reference kinase activity profile
representing the kinase activity profile being representative
for a good responder or a poor responder to said medica-
ment;
  (ii.2) finding a deviation or no deviation of the kinase
activity profile as determined in (a) from said reference
kinase activity profile; and
  (iii.2) attributing said finding of deviation or no deviation
to a particular response of said patient diagnosed with
NSCLC to said medicament.
  In particular embodiments, step (b) of predicting from
said kinase activity profile the response of said patient to
treatment with said PD-1 or PD-L1 ICI comprises a step (i.3)
of comparing said kinase activity profile to a reference
kinase activity profile; said reference kinase activity profile
representing a known sensitivity (or responsiveness or sus-
ceptibility) to said PD-1 or PD-L1 ICI; and a step (ii.3) of
predicting the response of said patient to said PD-1 or PD-L1
ICI on the basis of the comparison of said kinase activity
profile with said reference kinase activity profile.
  For example, a reference kinase activity profile may
represent a known sensitivity to treatment with a PD-1 or PD-L1 ICI in the patient, such as the determination that the
patient will be sensitive to treatment with a PD-1 or PD-L1
ICI, or the determination that the patient will be resistant to
treatment with a PD-1 or PD-L1 ICI. In another example, a
reference kinase activity profile may represent responders to
treatment with a PD-1 or PD-L1 ICI or non-responders to
treatment with a PD-1 or PD-L1 ICI. In yet another example,
a reference kinase activity profile may represent a determi-
nation of a certain degree of sensitivity to treatment with a
PD-1 or PD-L1 ICI in the patient.
  In particular embodiments, said reference kinase activity
profile represents a known sensitivity (or responsiveness or
susceptibility) of a reference subject to treatment with said
PD-1 or PD-L1 ICI. In particular embodiments, said refer-
ence kinase activity profile may correspond to the kinase
activity profile in a blood sample comprising peripheral
blood mononuclear cells from one or more a reference
subjects who are sensitive (or responsive, susceptible, or a
good responder) to treatment with said PD-1 or PD-L1 ICI.
In particular embodiments, said reference kinase activity
profile may correspond to the kinase activity profile in a
blood sample comprising peripheral blood mononuclear
cells from a one or more reference subjects who are insen-
sitive (or unresponsive, insusceptible, or a poor responder)
to treatment with said PD-1 or PD-L1 ICI.
  Reference kinase activity profiles may be established
according to known procedures. For example, a reference
kinase activity profile may be established in a reference
subject or individual or a population of individuals charac-
terized by a particular determination of sensitivity (or
responsiveness) to treatment with a PD-1 or PD-L1 ICI (i.e.,
for whom said determination of sensitivity (or responsive-
ness) to treatment a PD-1 or PD-L1 ICI holds true). Such
population may comprise without limitation 2 or more, 10 or
more, 100 or more, or even several hundred or more
individuals. In certain embodiments, the reference subjects
are subjects with the same type of neoplastic disease (i.e.
NSCLC), e.g., to not compare different types of neoplastic
diseases, and/or subjects with the same stage of NSCLC and
have been treated with the same neoplastic agent or neo-
plastic agents including a PD-1 or PD-L1 ICI.
  A "deviation" of a first value from a second value may
generally encompass any direction (e.g., increase: first
value>second value; or decrease: first value<second value)
and any extent of alteration.
  For example, a deviation may encompass a decrease in a
first value by, without limitation, at least about 10% (about
0.9-fold or less), or by at least about 20% (about 0.8-fold or
less), or by at least about 30% (about 0.7-fold or less), or by
at least about 40% (about 0.6-fold or less), or by at least
about 50% (about 0.5-fold or less), or by at least about 60%
(about 0.4-fold or less), or by at least about 70% (about
0.3-fold or less), or by at least about 80% (about 0.2-fold or
less), or by at least about 90% (about 0.1-fold or less),
relative to a second value with which a comparison is being
made.
  For example, a deviation may encompass an increase of
a first value by, without limitation, at least about 10% (about
1.1-fold or more), or by at least about 20% (about 1.2-fold
or more), or by at least about 30% (about 1.3-fold or more),
or by at least about 40% (about 1.4-fold or more), or by at
least about 50% (about 1.5-fold or more), or by at least about
60% (about 1.6-fold or more), or by at least about 70%
(about 1.7-fold or more), or by at least about 80% (about
1.8-fold or more), or by at least about 90% (about 1.9-fold
or more), or by at least about 100% (about 2-fold or more),
or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$ or $\pm 3 \times SD$, or $\pm 1 \times SE$ or $\pm 2 \times SE$ or $\pm 3 \times SE$). Deviation may also refer to a value falling outside of a reference range defined by values in a given population (for example, outside of a range which comprises $\geq 0\%$, $\geq 50\%$, $\geq 60\%$, $\geq 70\%$, $\geq 75\%$ or $\geq 89\%$ or $\geq 85\%$ or $\geq 90\%$ or $\geq 95\%$ or even $\geq 100\%$ of values in said population).

In particular embodiments, said deviation may be concluded if said deviation has a statistical significance of $p<0.05$.

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

In particular embodiments, step (b) of the method for predicting the response of a patient diagnosed with NSCLC to a medicament as taught herein (i.e. the step of determining from said kinase activity profile the response of said patient to said medicament) comprises a step (i.4) of calculating a classifier parameter from said kinase activity profile; and a step (ii.4) of determining the response of said patient to said medicament on the basis of said classifier parameter.

Accordingly, in a particular embodiment, the present invention relates to a method for predicting the response of a patient diagnosed with NSCLC cancer, to a medicament, comprising the steps of:

(a) measuring the kinase activity of
at least one kinase of the VEGFR or PDGFR family of kinases, preferably at least one kinase of the VEGFR or PDGFR family of kinases selected from the group consisting of FLT1, FLT3 and FLT4;
at least one kinase of the Src family of kinases, preferably at least one kinase of the Src family of kinases selected from the group consisting of Src, BLK, LCK, Fyn, and YES; and
at least one kinase of the Syk family of kinases, preferably at least one kinase of the Syk family of kinases selected from the group consisting of Syk and ZAP70,
in a blood sample obtained from said patient diagnosed with NSCLC thereby providing a kinase activity profile of said blood sample
(i.4) calculating a classifier parameter from said kinase activity profile; and
(ii.4) determining the response of said patient to said medicament on the basis of said classifier parameter.

By establishing a classifier parameter for determining the prediction of pharmacotherapy response of the NSCLC patient the method of the present invention provides a criterion for analysing the results obtained from the method of the present invention. This criterion enables a person to provide a prediction or prognosis on the basis of a single or limited number of data. The person providing the prediction or prognosis does not have to interpret an entire set of data, but rather bases his conclusion on the basis of a single or limited number of criteria.

The term "classifier parameter" as used herein is a discriminating value which has been determined by establishing the kinase activity profile and/or phosphorylation profile of a sample obtained from a patient suffering from NSCLC. Said discriminating value identifies the prediction of response to pharmacotherapy of NSCLC patients. The classifier parameter includes information regarding the activity of several kinases and/or the phosphorylation level of several protein kinase substrates. Classification is a procedure in which individual items are placed into groups based on quantitative information on one or more characteristics inherent in the items (e.g. kinase activity profile of a sample and/or phosphorylation levels or profiles of a sample) and based on a training set of previously labelled items (clinical response to a pharmacotherapy). The classifier parameter is calculated by applying a "classifier" to the measured kinase activity and/or phosphorylation levels of a sample. Based on the classifying parameter a sample is assigned to (or predicted to belong to) a class (predicting the pharmacotherapy response of said patient). The classifier has been previously determined by comparing samples which are known to belong to the respective relevant classes. Several methods are known in the art for developing a classifier including the neural network (Multi-layer Perceptron), support vector machines, k-nearest neighbours, Gaussian mixture model, naive bayes, decision tree, RBF classifiers, random forest, discriminant analysis, linear discriminant analysis, quadratic discriminant analysis, discriminant analysis—principal component analysis, partial least squares discriminant analysis, generalized distance regression and elastic net classification. The classifier parameter determined in this manner is valid for the same experimental setup in future individual tests.

It is not relevant to give an exact threshold value for the classifier parameter. A relevant threshold value can be obtained by correlating the sensitivity and specificity and the sensitivity/specificity for any threshold value. A threshold value resulting in a high sensitivity results in a lower specificity and vice versa. If one wants to increase the positive predictive value of the test to determine whether NSCLC patient will respond to targeted pharmacotherapy, then the threshold value of the test can be changed which as a consequence will decrease the negative predictive value of the test to determine whether NSCLC patient will not respond to targeted pharmacotherapy. If one wants to increase the negative predictive value of the test to determine whether NSCLC patient will not respond to targeted pharmacotherapy, then the threshold value can be changed in the opposite direction which as a consequence will decrease the positive predictive value of the test to determine whether NSCLC patient will respond to targeted pharmacotherapy.

It is thus up to the diagnostic engineers to determine which level of positive predictive value/negative predictive value/sensitivity/specificity is desirable and how much loss in positive or negative predictive value is tolerable. The chosen threshold level could be dependent on other diagnostic parameters used in combination with the present method by the diagnostic engineers.

In yet another embodiment, the present invention relates to a method according to the present invention wherein said classifier parameter predicts the response of said patient to said medicament if said classifier parameter is above a first predetermined threshold level, and wherein said classifier parameter indicates non-response to said medicament of said patient if said classifier parameter is below a second predetermined threshold level.

According to another embodiment, the present invention relates to the method of the present invention wherein said differential kinase activity level or said classifier parameter indicates a response, no-response or undetermined or intermediate prediction of said medicament or the effect of the targeted pharmacotherapy of said patient.

In more particular embodiments, the kinase activity profile as determined in (a) indicates a good response of said patient to said medicament if the kinase activity of FLT3, FLT1, FLT4, HER4, JAK2 and/or TRKB is higher compared to a reference kinase activity of said kinases representing a poor responder; and/or the kinase activity of BLK, Fyn, Lck, Src, Syk and/or ZAP70, is lower compared to a reference kinase activity of said kinases representing a poor responder.

Alternatively, in more particular embodiments, the kinase activity profile as determined in (a) indicates a poor response of said patient to said medicament if the kinase activity of FLT3, FLT1, FLT4, HER4, JAK2 and/or TRKB is lower compared to a reference kinase activity of said kinases representing a good responder; and/or the kinase activity of BLK, Fyn, Lck, Src, Syk and/or ZAP70, is higher compared to a reference kinase activity of said kinases representing a good responder.

As used in the present application the prediction of response to targeted pharmacotherapy of NSCLC patients is generally divided into two types of non-responders and responders and additionally some undetermined or intermediate responders. Whereas responders to a targeted pharmacotherapy will survive longer or have additional clinical benefits (e.g. improved quality of life, prolonged progression free survival, etc.) due to the treatment, the non-responders or the patients developing resistance to a targeted pharmacotherapy will not benefit from the targeted pharmacotherapy. The method of the present invention specifically enables the distinction between responders (e.g. complete response (CR), partial response (PR), stable disease (SD)) and non-responders (e.g. progressive disease (PD)) to a targeted pharmacotherapy or between patients with an early (e.g. <140 days after initiation of therapy) and late (e.g. >140 days after initiation of therapy) progression of disease upon treatment with a targeted pharmacotherapy.

The kinase activity of at least one of the kinases listed in Table 1 and/or the at least one member of the TAM family of RTKs may be determined by any means known in the art to determine kinase activity.

For measuring the kinase activity of the sample a large variety of methods and formats are known in the art.

The activation state of a kinase and/or a substantial fraction of the entire kinome can be measured using, for example, macroarrays, microarrays, antibody-based arrays, mass spectrometry (MS), reverse-phase protein arrays, kinase activity assay for kinome profiling (KAYAK) methodology, the KiNativ platform, bead arrays (e.g. kinobeads), PamChip method, Pepscan Presto method, ELISA and multiplex ELISA techniques, blotting methods, surface plasmon resonance, capillary electrophoresis and FACS based cell sorting. More particularly, antibody-based arrays may be used to determine the level of phosphorylated proteins and protein kinases; mass spectrometry (MS)-based approaches can be used to investigate the activity of the kinome;

reverse-phase protein arrays include arrays which use cellular lysates that are immobilized on an array platform and which then are probed with specific phospho-antibodies; kinase activity assay for kinome profiling (KAYAK) methodology may use known substrate preferences of various protein kinases that are dictated by motifs surrounding the site of phosphorylation; the KiNativ platform may use specific beads to pull down kinases which can be combined with MS; kinobeads (i.e. beads linked to kinase inhibitors) can act as traps for activated kinases present in the samples; the PamChip method can profile activity of kinases using a flow-through peptide-microarray platform; the Pepscan Presto method can use peptide immobilized to glass surfaces and detection using radioactive 33p incorporation based on activity of kinases; ELISA formats can allow for high-throughput screening of activity of kinases using immobilized phosphospecific antibodies in kinase inhibitors; and FACS based cell sorting combined with intracellular probes can identify phosphorylated proteins and protein kinases.

In particular embodiments, said kinase activity is determined by contacting the sample with at least one protein kinase substrate, thereby providing a phosphorylation profile of said sample. In more particular embodiments, said kinase activity is determined by contacting the sample with at least one protein kinase substrate, thereby providing a phosphorylation profile of said sample, said phosphorylation profile comprising the phosphorylation levels of phosphorylation sites present in all 93 peptide markers as listed in Table 2.

As used in the present invention, the term "phosphorylation profile" refers to a data set representative for the phosphorylation levels of, preferably one or more, phosphorylation sites present on the protein kinase substrates. If the kinase activity of the kinases as taught herein is determined by contacting the sample with at least one protein kinase substrate a specific phosphorylation profile is obtained. The phosphorylation profile is generated by the phosphorylation of the protein kinase substrates with the protein kinases present in the sample and it comprises the level of phosphorylation of the phosphorylation sites present on the protein kinase substrates used. A phosphorylation profile can thus be generated when using at least one protein kinase substrate in different test conditions such as for example by comparing the phosphorylation of a sample on one peptide or protein (protein kinase substrate) in the presence and absence of a phosphatase modulating compound or medicament. More frequently phosphorylation profiles of a sample will be measured using several protein kinase substrates in the same or sequentially carried out experiments. Preferably, the present invention determines tyrosine, serine and threonine kinase activity levels or profiles.

It should be noted that a person skilled in the art will appreciate that the methods of the present invention can use phosphorylation profiles as a basis for determining protein kinase activity. However, the phosphorylation levels of individual protein kinase substrates can also be used as a basis for determining protein kinase activity.

The person skilled in the art will understand how to determine from said phosphorylation profile of said sample a kinase activity profile reflecting the kinase activity of at least one kinase of the VEGFR or PDGFR family of kinases, preferably at least one kinase of the VEGFR or PDGFR family of kinases selected from the group consisting of FLT1, FLT3 and FLT4;

at least one kinase of the Src family of kinases, preferably at least one kinase of the Src family of kinases selected from the group consisting of Src, BLK, LCK, Fyn, and YES; and at least one kinase of the Syk family of kinases, preferably at least one kinase of the Syk family of kinases selected from the group consisting of Syk and ZAP70.

For example, the kinase activity profile can be determined from said phosphorylation profile of said sample using upstream kinase analysis. This may be achieved by using information from knowledge databases (e.g. HRPD, PhosphoSite, Reactome and PhosphoNET).

Similar to the classifier parameter calculated from the kinase activity as taught herein, a classifier parameter can also be calculated from the phosphorylation levels of a sample. These classifier parameters calculated from the phosphorylation levels of a sample can be used to determine the kinase activity from the phosphorylation profile.

It should be noted that for the measurement of the protein kinase activity, ATP or any other phosphate source needs to be added to the sample when it is contacted with the protein kinase substrates. The presence of ATP will lead to a phosphorylation of the protein kinase substrates. Alternatively, the phosphorylation of the protein kinase substrates can be performed in the absence of exogenous ATP. When no ATP is added during the incubation of the sample with the protein kinase substrates, the endogenous ATP, the ATP naturally present in the sample, will act as the primary source of ATP.

The phosphorylation level of each of the protein kinase substrates can be monitored using any method known in the art. The response of the protein kinase substrates is determined using a detectable signal, said signal resulting from the interaction of the sample with the protein kinase substrates or by for instance measuring mass differences using mass spectrometry. In determining the interaction of the sample with the protein kinase substrates the signal is the result of the interaction of the phosphorylated substrates with a molecule capable of binding to the phosphorylated substrates. This binding can be detected by e.g. surface plasmon resonance or by the molecule being detectably labelled. For the latter, the molecule that specifically binds to the substrates of interest (e.g. antibody or polynucleotide probe) can be detectably labelled by virtue of containing an atom (e.g. radionuclide), molecule (e.g. fluorescein), or enzyme or particle or complex that, due to a physical or chemical property, indicates the presence of the molecule. A molecule may also be detectably labelled when it is covalently bound to or otherwise associated with a "reporter" molecule (e.g. a biomolecule such as an enzyme) that acts on a substrate to produce a detectable atom, molecule or other complex.

Detectable labels suitable for use in the present invention include any composition detectable by spectroscopic, photochemical, biochemical, immunochemical, electrical, optical or chemical means. Labels useful in the present invention include biotin for staining with labelled avidin or streptavidin conjugate, magnetic beads (e.g. Dynabeads'), fluorescent dyes (e.g. fluorescein, fluorescein-isothiocyanate (FITC), Texas red, rhodamine, green fluorescent protein, enhanced green fluorescent protein and related proteins with other fluorescence emission wavelengths, lissamine, phycoerythrin, Cy2, Cy3, Cy3.5, Cy5, Cy5.5, Cy7, FluorX [Amersham], SYBR Green I & II [Molecular Probes], and the like), radiolabels (e.g. 3H, 125I, 35S, 14C, or 32P), enzymes (e.g. luciferases, hydrolases, particularly phosphatases such as alkaline phosphatase, esterases and glycosidases, or oxidoreductases, particularly peroxidases such as horse radish peroxidase, and the like), substrates, cofactors, chemilluminescent groups, chromogenic agents, and colorimetric labels such as colloidal gold or coloured glass or plastic (e. g.

polystyrene, polypropylene, latex, etc.), protein particles or beads. In particular, all detectable labels well known to those skilled in the art may be used as detectable labels for use in the present invention.

Means of detecting such labels are well known to those of skill in the art. Thus, for example, chemiluminescent and radioactive labels may be detected using photographic film or scintillation counters, and fluorescent markers may be detected using a photodetector to detect emitted light (e.g. as in fluorescence-activated cell sorting). Enzymatic labels are typically detected by providing the enzyme with a substrate and detecting a coloured reaction product produced by the action of the enzyme on the substrate. Colorimetric labels are detected by simply visualizing the coloured label. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the colour associated with the label. Fluorescence resonance energy transfer has been adapted to detect binding of unlabeled ligands, which may be useful on arrays.

In a particular embodiment of the present invention the response of the protein kinase substrates to the sample is determined using detectably labelled antibodies; more in particular fluorescently labelled antibodies. In those embodiments of the invention where the substrates consist of protein kinase substrates, the response of the protein kinase substrates is determined using fluorescently labelled anti-phosphotyrosine antibodies, fluorescently labelled anti-phosphoserine or fluorescently labelled anti-phosphothreonine antibodies. The use of fluorescently labelled anti-phosphotyrosine antibodies or fluorescently labelled anti-phosphoserine or fluorescently labelled anti-phosphothreonine antibodies in the method of the present invention, allows real-time or semi real-time determination of the protein kinase activity and accordingly provides the possibility to express the protein kinase activity as the initial velocity of protein kinase derived from the activity over a certain period of incubation of the sample on the substrates.

The term "peptide markers" in the context of the present invention refers to the fact that the peptides as listed in Table 2 can be preferably used according to the methods of the present invention to measure the phosphorylation levels of phosphorylation sites of said markers in samples. The phosphorylation levels of the individual phosphorylation sites present in said markers may be measured and compared in different ways. Therefore the present invention is not limited to the use of peptides identical to any of these peptide markers as listed in Table 2 as such. The skilled person may easily on the basis of the peptide markers listed in Table 2 design variant peptides compared to the specific peptides in said Table and use such variant peptides in a method for measuring phosphorylation levels of phosphorylation sites common to said peptide markers as listed in Table 2. These variant peptides may have one or more (2, 3, 4, 5, 6, 7, etc.) amino acids more or less than the given peptides and may also have amino acid substitutions (preferably conservative amino acid substitutions) as long as these variant peptides retain at least one or more of the phosphorylation sites of said original peptides as listed in said tables. Further the skilled person may also easily carry out the methods according to the present invention by using proteins (full length or N- or C-terminally truncated) comprising the amino acid regions of the "peptide markers" listed in Table 2 as sources for studying the phosphorylation of sites present in the amino acid regions of the peptides listed in Table 2. Also the skilled person may use peptide mimetics.

The protein kinase substrates as used in the methods described herein, are meant to include peptides, proteins or peptide mimetics comprising, preferably one or more, of the phosphorylation sites of the peptide markers of Table 2. Said one or more phosphorylation sites are specifically phosphorylated by the protein kinases present in the sample thereby providing a phosphorylation profile. More preferably the protein kinase substrates (peptides, proteins or peptide mimetics) as used in the method of the present invention comprise or consists of all of the peptide markers listed in Table 2.

TABLE 2 list of 93 peptide markers comprising phosphorylation sites used for determining the kinase activity of the kinases as listed in Table 1, their sequence and SEQ ID NO. The name of the peptide markers refers to the associated proteins and to the start and the end position of the amino acid sequence.

| SEQ ID NO | Name | Sequence |
|---|---|---|
| 1 | 41_654_666 | LDGENIYIRHSNL |
| 2 | ACHD_383_395 | YISKAEEYFLLKS |
| 3 | ANXA1_14_26 | IENEEQEYVQTVK |
| 4 | ANXA2_17_29 | HSTPPSAYGSVKA |
| 5 | B3AT_39_51 | TEATATDYHTTSH |
| 6 | CTNB1_79_91 | VADIDGQYAMTRA |
| 7 | PGFRB_1014_1028 | PNEGDNDYIIPLPDP |
| 8 | CALM_95_107 | KDGNGYISAAELR |
| 9 | CBL_693_705 | EGEEDTEYMTPSS |
| 10 | CD3Z_116_128 | KDKMAEAYSEIGM |
| 11 | CD3Z_146_158 | STATKDTYDALHM |
| 12 | CDK7_157_169 | GLAKSFGSPNRAY |
| 13 | CRK_214_226 | GPPEPGPYAQPSV |
| 14 | DCX_109_121 | GIVYAVSSDRFRS |
| 15 | DDR1_506_518 | LLLSNPAYRLLLA |
| 16 | DYR1A_212_224 | KHDTEMKYYIVHL |
| 17 | DYR1A_312_324 | CQLGQRIYQYIQS |
| 18 | EGFR_1103_1115 | GSVQNPVYHNQPL |
| 19 | EGFR_1118_1130 | APSRDPHYQDPHS |
| 20 | EGFR_1165_1177 | ISLDNPDYQQDFF |
| 21 | EGFR_1190_1202 | STAENAEYLRVAP |
| 22 | EPHA1_774_786 | LDDFDGTYETQGG |

TABLE 2-continued list of 93 peptide markers comprising phosphorylation sites used for determining the kinase activity of the kinases as listed in Table 1, their sequence and SEQ ID NO. The name of the peptide markers refers to the associated proteins and to the start and the end position of the amino acid sequence.

| SEQ ID NO | Name | Sequence |
|---|---|---|
| 23 | EPHA4_589_601 | LNQGVRTYVDPFT |
| 24 | EPHA7_607_619 | TYIDPETYEDPNR |
| 25 | EPHB1_771_783 | DDTSDPTYTSSLG |
| 26 | EPHB4_583_595 | IGHGTKVYIDPFT |
| 27 | EPOR_361_373 | SEHAQDTYLVLDK |
| 28 | EPOR_419_431 | ASAASFEYTILDP |
| 29 | ERBB2_1241_1253 | PTAENPEYLGLDV |
| 30 | ERBB2_870_882 | LDIDETEYHADGG |
| 31 | ERBB4_1181_1193 | QALDNPEYHNASN |
| 32 | ERBB4_1277_1289 | IVAENPEYLSEFS |
| 33 | FAK1_569_581 | RYMEDSTYYKASK |
| 34 | FAK2_572_584 | RYIEDEDYYKASV |
| 35 | FER_707_719 | RQEDGGVYSSSGL |
| 36 | FES_706_718 | REEADGVYAASGG |
| 37 | FGFR1_761_773 | TSNQEYLDLSMPL |
| 38 | FGFR2_762_774 | TLTTNEEYLDLSQ |
| 39 | FGFR3_753_765 | TVTSTDEYLDLSA |
| 40 | INSR_992_1004 | YASSNPEYLSASD |
| 41 | JAK1_1015_1027 | AIETDKEYYTVKD |
| 42 | JAK2_563_577 | VRREVGDYGQLHETE |
| 43 | K2C6B_53_65 | GAGFGSRSLYGLG |
| 44 | K2C8_425_437 | SAYGGLTSPGLSY |
| 45 | KSYK_518_530 | ALRADENYYKAQT |
| 46 | LAT_194_206 | MESIDDYVNVPES |
| 47 | LAT_249_261 | EEGAPDYENLQEL |
| 48 | LCK_387_399 | RLIEDNEYTAREG |
| 49 | MBP_198_210 | ARTAHYGSLPQKS |
| 50 | MET_1227_1239 | RDMYDKEYYSVHN |
| 51 | MK01_180_192 | HTGFLTEYVATRW |
| 52 | MK07_211_223 | AEHQYFMTEYVAT |
| 53 | MK10_216_228 | TSFMMTPYVVTRY |
| 54 | MK12_178_190 | ADSEMTGYVVTRW |
| 55 | NTRK2_696_708 | GMSRDVYSTDYYR |
| 56 | ODBA_340_352 | DDSSAYRSVDEVN |

TABLE 2-continued list of 93 peptide markers comprising
phosphorylation sites used for determining
the kinase activity of the kinases
as listed in Table 1, their sequence and
SEQ ID NO. The name of the peptide markers
refers to the associated proteins and to the
start and the end position of the amino
acid sequence.

| SEQ ID NO | Name | Sequence |
|---|---|---|
| 57 | PP2AB_297_309 | EPHVTRRTPDYFL |
| 58 | PAXI_24_36 | FLSEETPYSYPTG |
| 59 | PDPK1_2_14 | ARTTSQLYDAVPI |
| 60 | PDPK1_369_381 | DEDCYGNYDNLLS |
| 61 | PECA1_706_718 | KKDTETVYSEVRK |
| 62 | PGFRB_1002_1014 | LDTSSVLYTAVQP |
| 63 | PGFRB_572_584 | VSSDGHEYIYVDP |
| 64 | PGFRB_709_721 | RPPSAELYSNALP |
| 65 | PGFRB_768_780 | SSNYMAPYDNYVP |
| 66 | PGFRB_771_783 | YMAPYDNYVPSAP |
| 67 | PRGR_786_798 | EQRMKESSFYSLC |
| 68 | PRRX2_202_214 | VVTASSPYSTVPPY |
| 69 | PTN11_539_551 | SKRKGHEYTNIKY |
| 70 | RAF1_332_344 | PRGQRDSSYYWEI |
| 71 | RASA1_453_465 | TVDGKEIYNTIRR |
| 72 | RB_804_816 | IYISPLKSPYKIS |
| 73 | RBL2_99_111 | VPTVSKGTVEGNY |
| 74 | RET_1022_1034 | TPSDSLIYDDGLS |
| 75 | RON_1346_1358 | SALLGDHYVQLPA |
| 76 | RON_1353_1365 | YVQLPATYMNLGP |
| 77 | SRC8_CHICK_470_482 | VSQREAEYEPETV |
| 78 | STAT4_714_726 | PSDLLPMSPSVYA |
| 79 | TEC_512_524 | RYFLDDQYTSSSG |
| 80 | TNNT1_2_14 | SDTEEQEYEEEQP |
| 81 | TYRO3_679_691 | KIYSGDYYRQGCA |
| 82 | VGFR1_1040_1052 | DFGLARDIYKNPD |
| 83 | VGFR1_1162_1174 | VQQDGKDYIPINA |
| 84 | VGFR1_1326_1338 | DYNSVVLYSTPPI |
| 85 | VGFR2_1046_1058 | DFGLARDIYKDPD |
| 86 | VGFR2_1052_1064 | DIYKDPDYVRKGD |
| 87 | VGFR2_1168_1180 | AQQDGKDYIVLPI |
| 88 | VGFR2_944_956 | RFRQGKDYVGAIP |
| 89 | VGFR2_989_1001 | EEAPEDLYKDFLT |
| 90 | VGFR3_1061_1073 | DIYKDPDYVRKGS |
| 91 | VINC_815_827 | KSFLDSGYRILGA |

TABLE 2-continued list of 93 peptide markers comprising
phosphorylation sites used for determining
the kinase activity of the kinases
as listed in Table 1, their sequence and
SEQ ID NO. The name of the peptide markers
refers to the associated proteins and to the
start and the end position of the amino
acid sequence.

| SEQ ID NO | Name | Sequence |
|---|---|---|
| 92 | ZAP70_485_497 | ALGADDSYYTARS |
| 93 | ZBT16_621_633 | LRTHNGASPYQCT |

It should further be noted that according to a preferred embodiment of the present invention the peptide markers as listed in Table 2 can be used as such for carrying out the methods according to the present invention. The present invention however also includes the use of analogs and combinations of these peptide markers for use in the method according to the present invention. The peptide marker analogs include peptide markers which show a sequence identity of more than 70%, preferably more than 80%, more preferably more than 90% and even more preferably more than 95%.

The medicament as used in the method of the present invention is a PD-1 immune checkpoint inhibitor or a PD-L1 immune checkpoint inhibitor. The PD-1 or PD-L1 immune checkpoint inhibitor can be any kind of chemical substance for instance used in the treatment, cure, prevention, or diagnosis of disease or used to otherwise enhance physical or mental well-being. Specifically said medicament can be an immunotherapeutic antibody directed against PD-1 (such as Nivolumab (e.g. Opdivo™) Pembrolizumab (e.g. Keytruda™), or Durvalumab (e.g. Imfinzi™)) or an immunotherapeutic antibody directed against PD-L1 (such as Atezolizumab (e.g. Tecentriq™), Avelumab (e.g. Bacencio™) and Cemiplimab (e.g. Libtayo™)).

In particular embodiments, the medicament as used in the method of the present invention is a PD-1 immune checkpoint inhibitor or a PD-L1 immune checkpoint inhibitor which is used in combination with an immune checkpoint inhibitor different from the PD-1 or PD-L1 immune checkpoint inhibitor, such as a CTLA-4 immune checkpoint inhibitor. Examples of such combination therapy include Nivolumab (PD-1 immune checkpoint inhibitor) and Ipilimumab (CTLA-4 immune checkpoint inhibitor).

As used herein, the term "immunotherapeutic antibody" refers to a type of antibody, preferably a monoclonal antibody, which binds to a specific cell or protein, preferably a cell surface protein, and thereby stimulates the immune system to attack those cells. The immunotherapeutic antibody is used in the treatment, cure, prevention, or diagnosis of disease or used to otherwise enhance physical or mental well-being.

As used herein, the term "immune checkpoint" refers to an inhibitory pathways hardwired into the immune system that is crucial for maintaining self-tolerance and modulating the duration and amplitude of physiological immune responses in peripheral tissues in order to minimize collateral tissue damage. Tumors can designate one or multiple immune-checkpoint pathways as a major mechanism of immune resistance, particularly against T cells that are specific for tumor antigens. Immune checkpoints can be blocked by antibodies. Examples of such immune check-points are CTLA-4, PD-1 and PD-L1.

More preferably the present invention relates to a method according to the present invention wherein said medicament is selected from the group consisting of Nivolumab (e.g. Opdivo™), Pembrolizumab (e.g. Keytruda™), Durvalumab (e.g. Imfinzi™) Atezolizumab (e.g. Tecentriq™), Avelumab (e.g. Bacencio™) and Cemiplimab (e.g. Libtayo™) and/or a combination thereof and/or analogues thereof. Even more preferably the present invention relates to a method according to the present invention wherein said medicament is Nivolumab or Pembrolizumab, and/or a combination thereof and/or analogues thereof. Even more preferably said medicament is Nivolumab, Another a further embodiment, the kinase substrates carrying phosphorylation sites according to the present invention are located or immobilized on a solid support, and preferably a porous solid support. Preferably said immobilized kinase substrates carrying phosphorylation sites will be immobilized proteins, peptides or peptide mimetics. More preferably, the peptides are immobilized on a solid support.

As used herein "peptide" refers to a short truncated protein generally consisting of 2 to 100, preferably 2 to 30, more preferably 5 to 30 and even more preferably 13 to 18 naturally occurring or synthetic amino acids which can also be further modified including covalently linking the peptide bonds of the alpha carboxyl group of a first amino acid and the alpha amino group of a second amino acid by eliminating a molecule of water. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds.

As used herein "protein" refers to a polypeptide made of amino acids arranged in a linear chain and joined together by peptide bonds between the carboxyl and amino groups of adjacent amino acid residues.

As used herein "peptide mimetics" refers to organic compounds which are structurally similar to peptides and similar to the peptide sequences list in Table 2. The peptide mimetics are typically designed from existing peptides to alter the molecules characteristics. Improved characteristics can involve, for example improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification.

Depending on the type of kinase activity measurement method the solid support on which the proteins, peptides or peptide mimetics are fixed may vary. Whereas in ELISA the protein kinase substrates are attached to the surface of the microtiterplates, in microarrays the protein kinase substrates are immobilized on and/or in the microarray substrate. Alternatively the substrates are synthesized in-situ direct on the microarray substrate.

In a preferred embodiment of the present invention the protein kinase a substrates are immobilized on an array, and preferably a microarray of protein kinase substrates wherein the protein kinase substrates are immobilized onto a solid support or another carrier. The immobilization can be either the attachment or adherence of two or more protein kinase substrate molecules to the surface of the carrier including attachment or adherence to the inner surface of said carrier in the case of e.g. a porous or flow-through solid support.

In a preferred embodiment of the present invention, the array of protein kinase substrates is a flow-through array. The flow-through array as used herein could be made of any carrier material having oriented through-going channels as are generally known in the art, such as for example described in PCT patent publication WO 01/19517. Typically the carrier is made from a metal oxide, glass, silicon oxide or cellulose. In a particular embodiment the carrier material is made of a metal oxide selected from the group consisting of zinc oxide, zirconium oxide, tin oxide, aluminium oxide, titanium oxide and thallium; in a more particular embodiment the metal oxide consists of aluminium oxide.

Accordingly, in a further embodiment of the present invention said array is a Pamchip®.

In a further embodiment, the present invention relates to a method according to the present invention wherein said solid support (microarray) comprises all 93 of the peptide markers as listed in Table 2 immobilized thereto.

In a further embodiment, the present invention relates to a method according to the present invention wherein said NSCLC is adenocarcinoma or squamous cell carcinoma.

In a further embodiment, the present invention relates to a method according to the present invention wherein said NSCLC is stage III NSCLC or stage IV NSCLC, preferably stage IV NSCLC.

In a further embodiment, the present invention relates to a method according to the present invention wherein said NSCLC is stage III adenocarcinoma or squamous cell carcinoma or stage IV adenocarcinoma or squamous cell carcinoma, preferably stage IV adenocarcinoma or squamous cell carcinoma.

Phosphorylation levels can also be measured according to the invention, without the necessity to generate phosphorylation profiles thereof. Also for this embodiment, the amount and the type of peptides, proteins or peptide mimetics to be used is as described above.

Another embodiment of the present invention regards the use of the method according to the present invention for assessing susceptibility of a patient having non-small-cell lung carcinoma to a medicament, wherein said medicament is a PD-1 or PD-L1 immune checkpoint inhibitor.

Another embodiment of the present invention regards the use of the method according to the present invention for assessing the pharmaceutical value of a medicament, wherein said medicament is a PD-1 or PD-L1 immune checkpoint inhibitor.

Another embodiment of the present invention regards the use of the method according to the present invention for assessing the clinical value of a medicament, wherein said medicament is a PD-1 or PD-L1 immune checkpoint inhibitor.

As used herein when assessing susceptibility to a drug, the pharmaceutical value of a drug or the clinical value of a drug, this comprises the assessment of the resistance of a subject or patient to said medicament, more particularly wherein said medicament is a PD-1 or PD-L1 immune checkpoint inhibitor.

The present invention also relates in another embodiment to a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out the method according to the present invention.

The present invention further relates to a computer system comprising a processor, and a memory coupled to said processor and encoding one or more programs, wherein said one or more programs instruct the processor to carry out the methods according to the present invention.

The present invention also relates in another embodiment to a kit for determining the response of a patient diagnosed with non-small-cell lung carcinoma to a medicament, comprising means for measuring the kinase activity of at least one, at least two, at least three, at least four, at least five, at least six, at least seven or at least eight kinases of the VEGFR or PDGFR family of kinases; preferably at least one, at least two, at least three, at least four, at least five, at least six, at least seven or all eight kinases of the VEGFR or PDGFR family of kinases selected from the group consisting of FLT1, FLT3, FLT4, CSF-1R, Kit, PDGFRalpha, PDGFRbeta and KDR; more preferably at least one, at least two, preferably all three, kinases of the VEGFR or PDGFR family of kinases selected from the group consisting of FLT1, FLT3 and FLT4;

at least one, at least two, at least three, at least four, at least five, at least six, at least seven, at least eight, at least nine, at least ten, or at least eleven kinases of the Src family of kinases; preferably at least one, at least two, at least three, at least four, at least five, at least six, at least seven, at least eight, at least nine, at least ten, or all eleven kinases of the Src family of kinases selected from the group consisting of Src, BLK, LCK, Fyn, YES, Brk, FGR, HCK, Lyn, FRK and Srms; more preferably at least one, at least two, at least three, at least four or all five kinases of the Src family of kinases selected from the group consisting of Src, BLK, LCK, Fyn, and YES; and at least one or at least two kinases of the Syk family of kinases, preferably two kinases of the Syk family of kinases selected from the group consisting of Syk and ZAP70, in a blood sample obtained from said patient diagnosed with NSCLC; and a computer readable storage medium having recorded thereon one or more programs for carrying out the method for predicting the response of a patient diagnosed with non-small-cell lung carcinoma, to a medicament as taught herein;

wherein said medicament is a PD-1 or PD-L1 immune checkpoint inhibitor; and wherein said blood sample comprises peripheral blood mononuclear cells.

In particular embodiments, the kit comprises means for measuring the kinase activity of FLT1, FLT3, FLT4, Src, BLK, LCK, Fyn, YES, Syk and ZAP70.

In more particular embodiments, the kit comprises means for measuring the kinase activity of FLT1, FLT3, FLT4, Src, BLK, LCK, Fyn, YES, Syk, ZAP70, JAK2, HER4 and TRKB.

The means for measuring the kinase activity of kinases of the VEGFR or PDGFR family of kinases, kinases of the Src family of kinases and kinases of the Syk family of kinases can be any means known in the art to determine kinase activity, such as an array comprising peptide markers.

In particular embodiments, the means for measuring the kinase activity of at least one, at least two, at least three, at least four, at least five, at least six, at least seven or at least eight kinases of the VEGFR or PDGFR family of kinases; preferably at least one, at least two, at least three, at least four, at least five, at least six, at least seven or all eight kinases of the VEGFR or PDGFR family of kinases selected from the group consisting of FLT1, FLT3, FLT4, CSF-1R, Kit, PDGFRalpha, PDGFRbeta and KDR; more preferably at least one, at least two, preferably all three, kinases of the VEGFR or PDGFR family of kinases selected from the group consisting of FLT1, FLT3 and FLT4;

at least one, at least two, at least three, at least four, at least five, at least six, at least seven, at least eight, at least nine, at least ten, or at least eleven kinases of the Src family of kinases; preferably at least one, at least two, at least three, at least four, at least five, at least six, at least seven, at least eight, at least nine, at least ten, or all eleven kinases of the Src family of kinases selected from the group consisting of Src, BLK, LCK, Fyn, YES, Brk, FGR, HCK, Lyn, FRK and Srms; more preferably at least one, at least two, at least three, at least four or all five kinases of the Src family of kinases selected from the group consisting of Src, BLK, LCK, Fyn, and YES; and at least one or at least two kinases of the Syk family of kinases, preferably two kinases of the Syk family of kinases selected from the group consisting of Syk and ZAP70, is at least one array comprising all of the 93 peptide markers as listed in Table 2.

In particular embodiments, the means for measuring the kinase activity of at least one, at least two, preferably all three, kinases of the VEGFR or PDGFR family of kinases selected from the group consisting of FLT1, FLT3 and FLT4;

at least two, at least three, at least four, preferably all five, kinases of the Src family of kinases selected from the group of consisting of Src, BLK, LCK, Fyn, and YES;

at least one, preferably all two, kinases of the Syk family of kinases selected from the group of kinases consisting of Syk and ZAP70;

is at least one array comprising all of the 93 peptide markers as listed in Table 2.

The present invention further relates in yet another embodiment to the use of the kinase activity of at least one, at least two, at least three, at least four, at least five, at least six, at least seven or at least eight kinases of the VEGFR or PDGFR family of kinases; preferably at least one, at least two, at least three, at least four, at least five, at least six, at least seven or all eight kinases of the VEGFR or PDGFR family of kinases selected from the group consisting of FLT1, FLT3, FLT4, CSF-1R, Kit, PDGFRalpha, PDGFRbeta and KDR; more preferably at least one, at least two, preferably all three, kinases of the VEGFR or PDGFR family of kinases selected from the group consisting of FLT1, FLT3 and FLT4;

at least one, at least two, at least three, at least four, at least five, at least six, at least seven, at least eight, at least nine, at least ten, or at least eleven kinases of the Src family of kinases; preferably at least one, at least two, at least three, at least four, at least five, at least six, at least seven, at least eight, at least nine, at least ten, or all eleven kinases of the Src family of kinases selected from the group consisting of Src, BLK, LCK, Fyn, YES, Brk, FGR, HCK, Lyn, FRK and Srms; more preferably at least one, at least two, at least three, at least four or all five kinases of the Src family of kinases selected from the group consisting of Src, BLK, LCK, Fyn, and YES; and at least one or at least two kinases of the Syk family of kinases, preferably two kinases of the Syk family of kinases selected from the group consisting of Syk and ZAP70, for predicting the response of a patient diagnosed with NSCLC cancer to a medicament, wherein said medicament is a PD-1 or PD-L1 immune checkpoint inhibitor.

In a particular embodiment, the present invention relates to the use of the kinase activity of FLT1, FLT3, FLT4, Src, BLK, LCK, Fyn, YES, Syk, and ZAP70 for predicting the response of a patient diagnosed with NSCLC cancer to a medicament, wherein said medicament is a PD-1 or PD-L1 immune checkpoint inhibitor.

In a further particular embodiment, the present invention relates to the use of the kinase activity of FLT1, FLT3, FLT4, Src, BLK, LCK, Fyn, YES, Syk, ZAP70, JAK2, HER4 and TRKB for predicting the response of a patient diagnosed with NSCLC cancer to a medicament, wherein said medicament is a PD-1 or PD-L1 immune checkpoint inhibitor.

Since the present inventors have identified a surprisingly useful set of kinases to be used in methods for determining the prediction of response to a targeted pharmacotherapy, more particularly to a PD-1 or PD-L1 immune checkpoint inhibitor, of a patient suffering from NSCLC, the skilled man may carry out any method as defined above wherein he measures the kinase activity of at least one, at least two, at least three, at least four, at least five, at least six, at least seven or at least eight kinases of the VEGFR or PDGFR family of kinases; preferably at least one, at least two, at least three, at least four, at least five, at least six, at least seven or all eight kinases of the VEGFR or PDGFR family of kinases selected from the group consisting of FLT1, FLT3, FLT4, CSF-1R, Kit, PDGFRalpha, PDGFRbeta and KDR; more preferably at least one, at least two, preferably all three, kinases of the VEGFR or PDGFR family of kinases selected from the group consisting of FLT1, FLT3 and FLT4;

at least one, at least two, at least three, at least four, at least five, at least six, at least seven, at least eight, at least nine, at least ten, or at least eleven kinases of the Src family of kinases; preferably at least one, at least two, at least three, at least four, at least five, at least six, at least seven, at least eight, at least nine, at least ten, or all eleven kinases of the Src family of kinases selected from the group consisting of Src, BLK, LCK, Fyn, YES, Brk, FGR, HCK, Lyn, FRK and Srms; more preferably at least one, at least two, at least three, at least four or all five kinases of the Src family of kinases selected from the group consisting of Src, BLK, LCK, Fyn, and YES; and at least one or at least two kinases of the Syk family of kinases, preferably two kinases of the Syk family of kinases selected from the group consisting of Syk and ZAP70.

Also this method may be carried out using the amount and type of peptides, proteins or protein mimetics as defined above. The formats for carrying out these methods are also as for the methods described above.

Also provided herein is a method of treating a patient diagnosed with NSCLC, comprising (I) determining the response of a patient diagnosed with NSCLC, to treatment with a PD-1 or PD-L1 ICI comprising the steps of (a) measuring the kinase activity of
   at least one kinase of the VEGFR or PDGFR family of kinases;
   at least one kinase of the Src family of kinases; and
   at least one kinase of the Syk family of kinases,
in a blood sample obtained from said patient diagnosed with NSCLC thereby providing a kinase activity profile of said blood sample; and (b) determining from said kinase activity profile the response of said patient to said medicament;

wherein said blood sample comprises peripheral blood mononuclear cells; and (II) treating said patient with said PD-1 or PD-L1 ICI if said patient is determined to be responsive to said PD-1 or PD-L1 ICI; or treating said patient with an antineoplastic therapy other than said PD-1 or PD-L1 ICI if said patient is determined to be unresponsive to said PD-1 or PD-L1 ICI.

Antineoplastic therapies other than said PD-1 or PD-L1 ICI to which the response is determined are well-known in the art. For example, when the NSCLC is characterized by a EGFR mutation, the antineoplastic therapy can be selected from the group consisting of osimertinib, erlotinib, afatinib, gefitinib, dacomitinib, and any combination thereof. For example, when the NSCLC is characterized by an ALK rearrangement the antineoplastic therapy can be selected from the group consisting of alectinib, brigatinib, ceritinib, crizotinib, and any combination thereof. For example, if the NSCLC is characterized by ROS1 rearrangements the antineoplastic therapy can be selected from the group consisting of crizotinib, ceritinib and a combination thereof. For example, if the NSCLC is characterized by a BRAF V600E mutation the antineoplastic therapy can be selected from the group consisting of dabrafenib, trametinib and a combination thereof. For example, if the NSCLC is characterized by a NTRK gene fusion mutation the antineoplastic therapy can be larotrectinib. For example, if the NSCLC is characterized by any other mutations than a EGFR mutation, an ALK rearrangement, a ROS1 rearragement, a BRAF V600E mutation or a NTRK gene fusion mutation, or if the NSCLC is characterized by no mutation, the antineoplastic therapy can be platinum-doublet chemotherapy potentially also including bevacizumab or other types of chemotherapy or docetaxel or pemetrexed or gemcitabine or ramucirumab including docetaxel. The person skilled in the art will understand that these antineoplastic treatment regimens further depend on the TNM stage of the NSCLC tumor, the performance score of the patient, the type of lung cancer, the line of therapy and the choices made by the individual patient and the treating physician.

In other words, the PD-1 or PD-1L ICI may be used in the treatment of NSCLC, comprising:

(I) determining the response of a patient diagnosed with NSCLC, to treatment with a PD-1 or PD-L1 ICI comprising the steps of (a) measuring the kinase activity of
   at least one kinase of the VEGFR or PDGFR family of kinases;
   at least one kinase of the Src family of kinases; and
   at least one kinase of the Syk family of kinases,
in a blood sample obtained from said patient diagnosed with NSCLC thereby providing a kinase activity profile of said blood sample; and (b) determining from said kinase activity profile the response of said patient to said medicament;

wherein said blood sample comprises peripheral blood mononuclear cells; and (II) administering said PD-1 or PD-L1 ICI to said patient if said patient is determined to be responsive to said PD-1 or PD-L1 ICI or not administering said PD-1 or PD-L1 ICI to said patient if said patient is determined to be unresponsive to said PD-1 or PD-L1 ICI.

The terms "treat" or "treatment" have their generally accepted meaning and preferably encompass both the therapeutic treatment of an already developed disease or condition, such as the therapy of an already developed neoplastic disease, as well as prophylactic or preventive measures, wherein the aim is to prevent or lessen the chances of incidence of an undesired affliction, such as to prevent occurrence, development and progression of a neoplastic disease. Beneficial or desired clinical results may include, without limitation, alleviation of one or more symptoms or one or more biological markers, diminishment of extent of disease, stabilized (i.e., not worsening) state of disease, delay or slowing of disease progression, amelioration or palliation of the disease state, and the like. "Treatment" can also mean prolonging survival as compared to expected survival if not receiving treatment.

The PD-1 or PD-L1 ICI for use and methods as taught herein allow to administer a therapeutically effective amount of a PD-1 or PD-L1 ICI, in patients diagnosed with NSCLC who will benefit from such treatment. The term "therapeutically effective amount" as used herein, has its generally accepted meaning and preferably refers to an amount of active compound or pharmaceutical agent that elicits the biological or medicinal response in a subject that is being sought by a surgeon, researcher, veterinarian, medical doctor or other clinician, which may include inter alia alleviation of the symptoms of the disease or condition being treated. Methods are known in the art for determining therapeutically effective doses of a PD-1 or PD-L1 ICI as taught herein.

In certain embodiments, said PD-1 or PD-L1 ICI is formulated into and administered as pharmaceutical formulations or compositions. Such pharmaceutical formulations or compositions may be comprised in a kit of parts.

The term "pharmaceutically acceptable" as used herein is consistent with the art and preferably means compatible with the other ingredients of a pharmaceutical composition and not deleterious to the recipient thereof.

As used herein, "carrier" or "excipient" has its generally accepted meaning and preferably includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

Illustrative, non-limiting carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

Pharmaceutical compositions as intended herein may be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous, intramuscular, intraperitoneal or intrasternal injection or infusion), transdermal or transmucosal (such as, e.g., oral, sublingual, intranasal) administration, topical administration, rectal, vaginal or intra-tracheal instillation, and the like. In this way, the therapeutic effects attainable by the methods and compositions can be, for example, systemic, local, tissue-specific, etc., depending of the specific needs of a given application.

The dosage or amount of the present PD-1 or PD-L1 ICI used, optionally in combination with one or more other active compounds to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the patient to be treated, on the route of administration, efficacy, metabolic stability and duration of action of the compounds used, on whether the therapy is acute or chronic or prophylactic, or on whether other active compounds are administered in addition to the PD-1 or PD-L1 ICI as described herein.

Without limitation, depending on the type and severity of the disease, a typical dosage of a PD-1 or PD-L1 ICI as disclosed herein, or combinations of two or more such PD-1 or PD-L1 las, might range from about 1 µg/kg to 1 g/kg of body weight or more, depending on the factors mentioned above. For instance, at an ICI treatment interval of 2 to 4 weeks a dosage of the agent(s) may range from about 0.5 mg/kg to 50 mg/kg of body weight or about 100-2000 mg per patient per treatment cycle. For repeated administrations over several weeks or months or longer, depending on the condition, the treatment is sustained until a desired suppression of disease symptoms occurs.

In certain embodiments, the a PD-1 or PD-L1 ICI may be administered at least once a month during the treatment, for example the PD-1 or PD-L1 ICI may be administered at least once every three weeks during the treatment, for example the a PD-1 or PD-L1 ICI may be administered at least once every two weeks during the treatment.

In certain embodiments, the PD-1 or PD-L1 ICI or pharmaceutical formulation as taught herein may be used alone or in combination with one or more active compounds that are suitable in the treatment of neoplastic diseases (i.e., combination therapy). The latter can be administered before, after, or simultaneously with the administration of the PD-1 or PD-L1 ICI or pharmaceutical formulation as taught herein.

The person skilled in the art will understand that the different embodiments of the methods for determining the response of a patient in need of an ICI to treatment with a PD-1 or PD-1L ICI are applicable to all methods (e.g. methods of treatment), uses, kits, computer program products and computer systems as described herein, and vice versa.

The present invention is hereafter exemplified by the illustration of particular, non-limiting examples.

EXAMPLES

Example 1. NSCLC Patients with Short Term Progression and Late (or no) Progression on Treatment with Nivolumab or Pembroluzimab can be Differentiated According to Kinase Activity Profiles (Peptide Microarray)

PBMCs were isolated from 56 NSCLC patients (comprising two sub-cohorts) shortly prior to treatment with Immuno Checkpoint Inhibitors (ICI). All patients received anti-PD1 mono therapy with Nivolumab or Pembroluzimab and were not treated with any prior line of immunotherapy. PBMCs were lysed in MPER buffer in the presence of protease and phosphatase inhibitors and 2 μg total protein was profiled for protein tyrosine kinase (PTK) activity using dynamic peptide microarrays (PamChip). The microarrays comprised 144 different peptides, being substrates for protein tyrosine kinases. The resulting phosphorylation profiles or kinase activity profiles were processed in R including a normalization step (variance stabilizing normalization, VSN) and a correction with the ComBat method for systematic differences between the two sub-cohorts.

The differential phosphorylation profiles or kinase activity profile between patients with early (Progression Free Survival (PFS)<140 days) vs late no progression (PFS>140 days) is shown in FIG. 1, showing average difference in phosphorylation of the 93 peptides (corresponding to the peptides as listed in Table 2) between the early progression group and the late/no progression group respectively. 18 phosphorylation sites were identified as being the most differentiating phosphorylation sites using a two sample t-test (data not shown).

Figure 2:
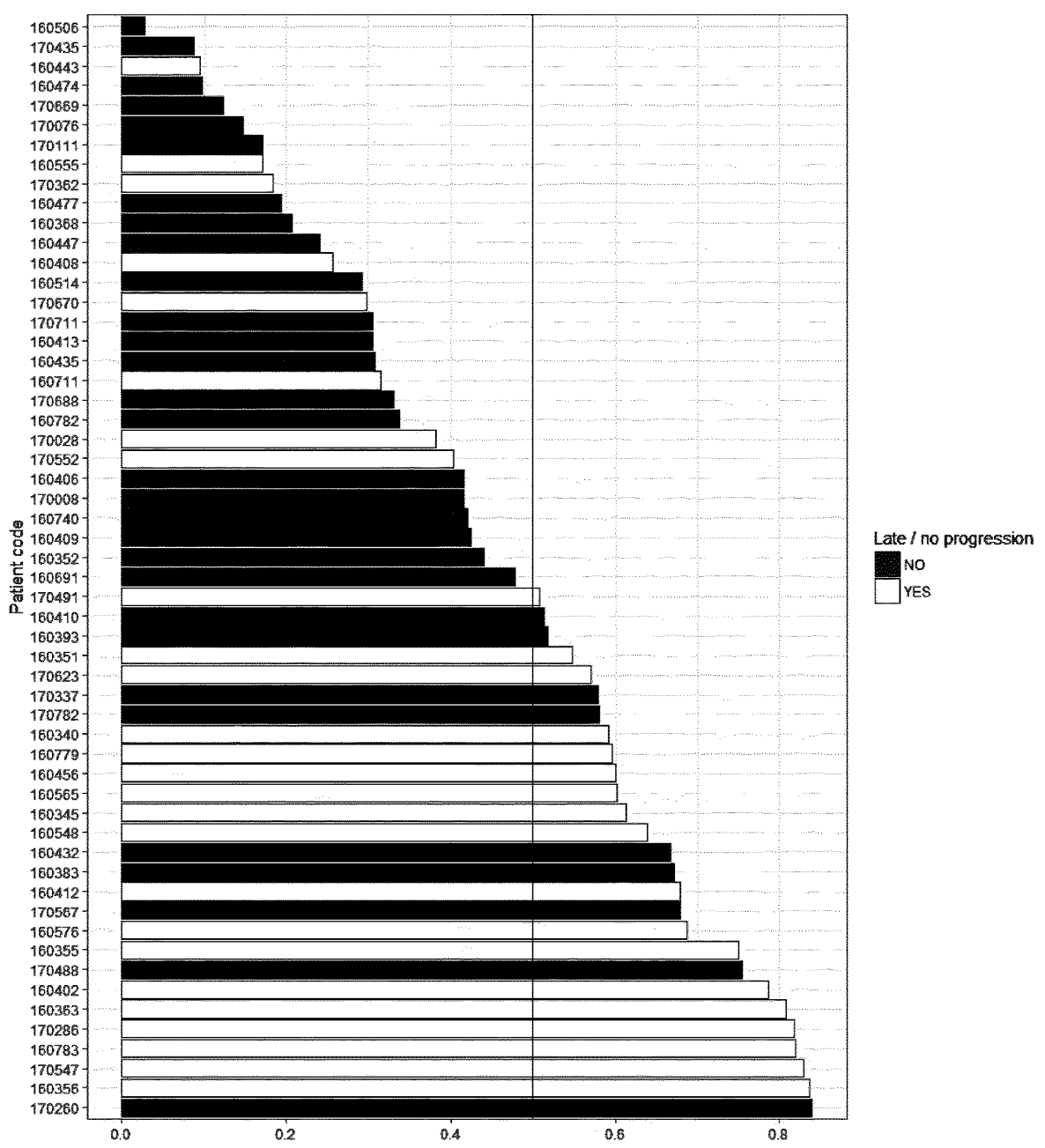
FIG. 2. (A) Class prediction analysis of the kinase activity profiles of the individual patients. Elastic net modeling (GLMnet) was used in R to train a predictive model for assigning a patient to the early progression or late/no progression class. Shown is for each included patient the predicted probability p (L/N) for belonging to the late/no progression class obtained by 20-fold cross validation. The fill color of the bar indicates the known class of the patients as indicated in the legend. It may be seen that patients with actual early progression ("black bars") tend to have lower predicted probabilities p(L/N) for belonging to the late/no progression group than the patients with an actual late/no progression ("white bars"). (B). Kaplan Meier plot showing the progression free survival (PFS) of the patients in the "predicted low-risk" group (dashed line, p(≤0.5). The "predicted high-risk" group showed a significantly poorer PFS (median PFS 56 vs. 246 days, p=0.02).
Figure 2:
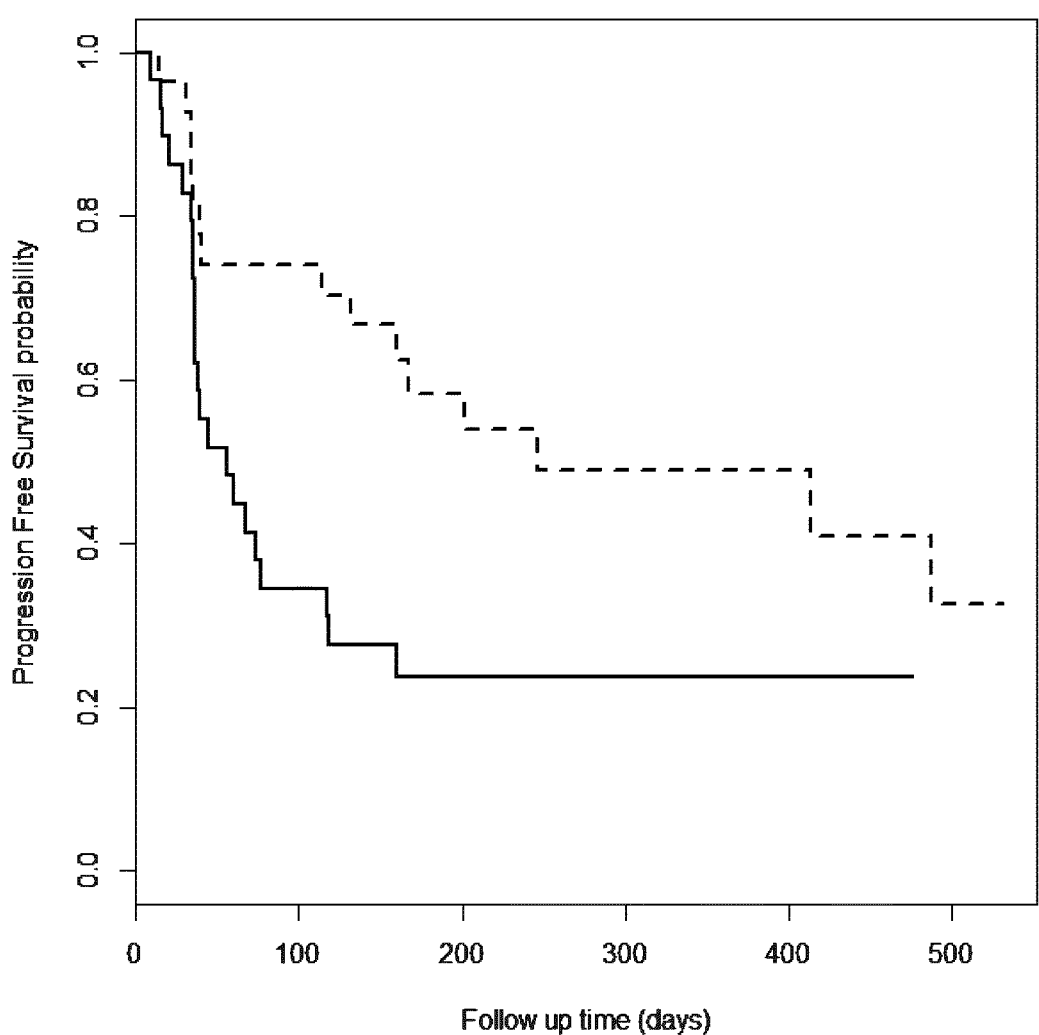

Surprisingly, the phosphorylation profiles or kinase activity profiles of the individual patients provided a good prediction of treatment outcome of patients treated with anti-PD1 ICI. Using GLMnet in R to train and evaluate a predictive model it was possible to divide patients with early progression versus late/no progression (FIG. 2A-B).

Figure 3:
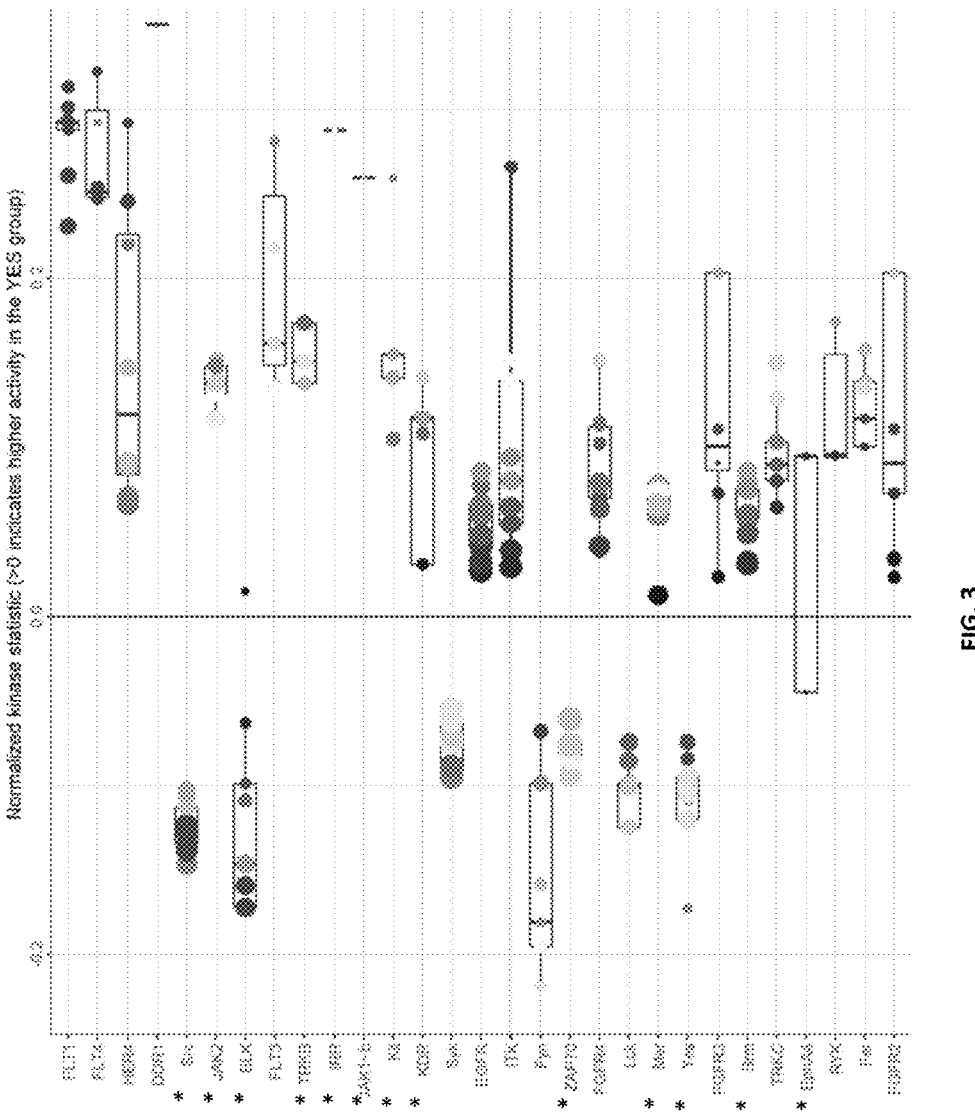
FIG. 3. Analysis identifying putative upstream kinases responsible for the differential phosphorylation of the peptides of FIG. 1 between the early progression and the late/no progression group. A positive value on the x-axis indicates that in the analysis the activity of the associated kinase is higher in the late/no progression group. The asterisks indicate the kinases as listed in Table 1.
Figure 3:
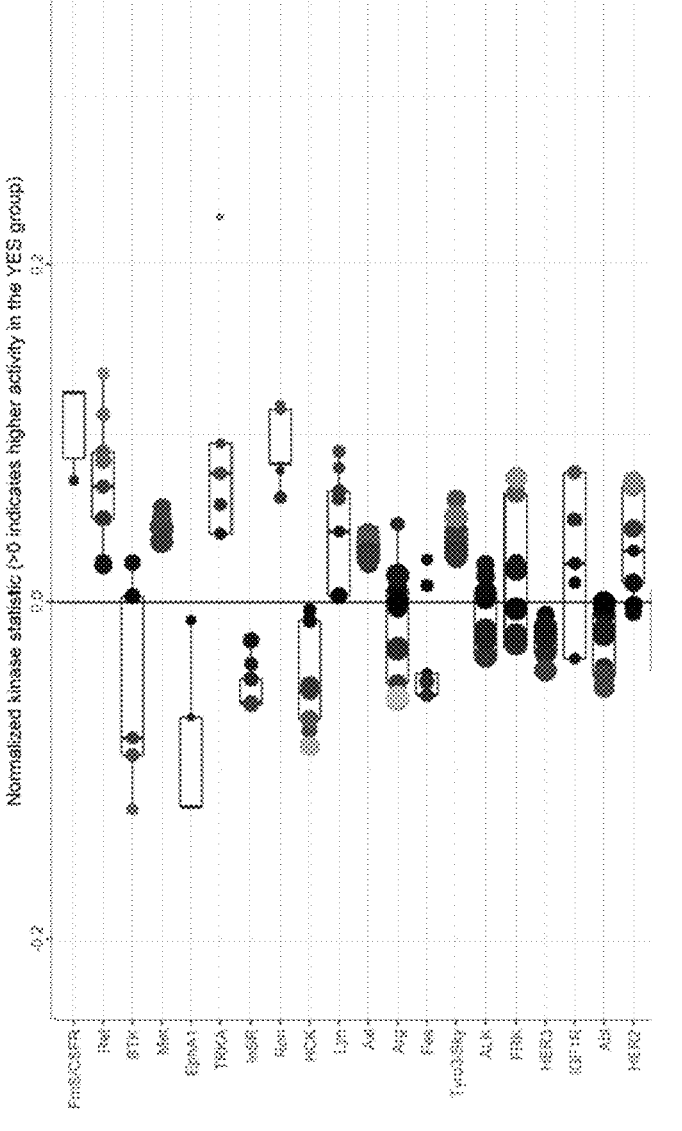
Figure 3:
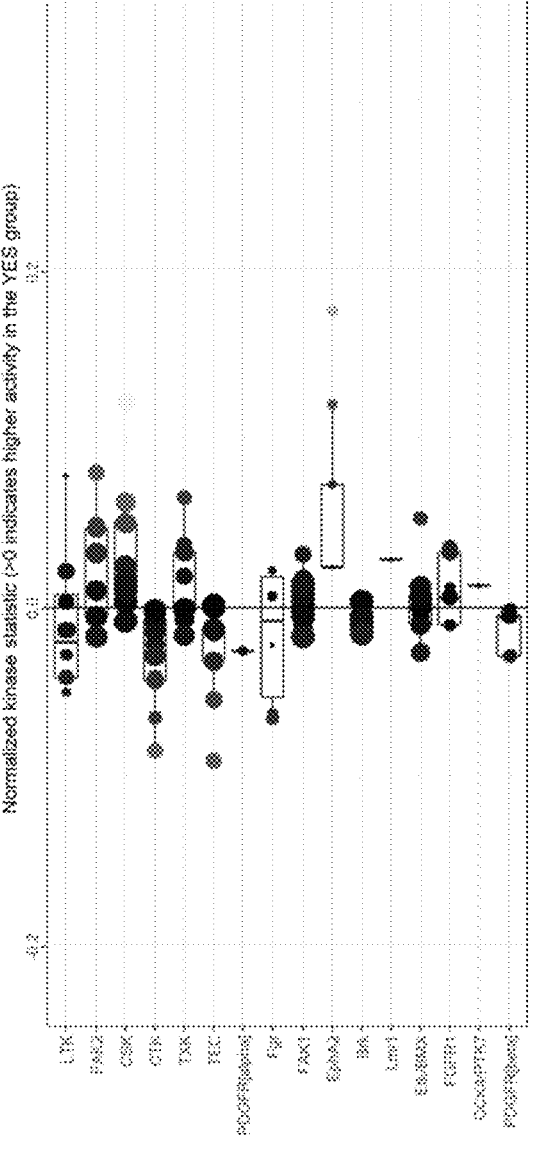
Figure 4:
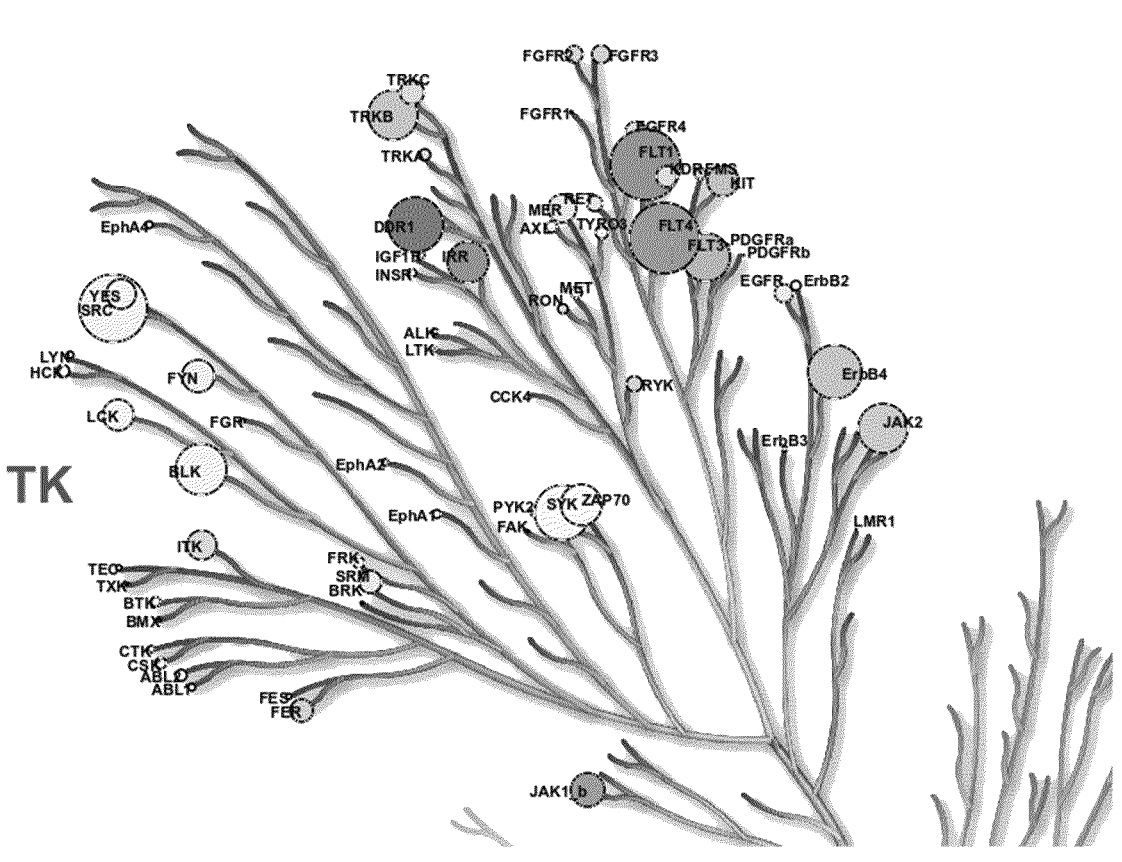
FIG. 4. Phylogenetic tree construction of the NSCLC cohort comparing patients with early progression with late/no progression. The size of the circles represent effect size.

The differential phosphorylation profile or kinase activity profile of patients with early versus patients with late/no progression combined with the corresponding peptide sequences were analyzed for putative upstream kinase activity which can induce the difference in phosphorylation between the two groups of patients. Information from knowledge databases (HPRD, PhosphoSite, Reactome, and PhosphoNET) is used to identify kinases that may act as markers for predicting the response of a patient to anti-PD1 ICI therapy (FIG. 3 and FIG. 4, which presents the same information as shown in FIG. 3 but shows the evolutionary relationships among the kinases). Tyrosine kinases that show a higher activity in this analysis for patients with late/no progression are kinases of the VEGFR and PDGFR family including FLT1, FLT3, FLT4 as well as other kinases including JAK2, HER4, and TRKB. Tyrosine kinases that show a higher activity in the analysis for patients with early progression are kinases from the Src family including Src, BLK, LCK, Fyn, and YES as well as the Syk family kinases Syk and ZAP70.

---

The invention claimed is:

1. A method of treating a patient diagnosed with non-small-cell lung carcinoma (NSCLC) with a medicament selected from the group consisting of a programmed death 1 (PD-1) immune checkpoint inhibitor or a programmed death-ligand 1 (PD-L1) immune checkpoint inhibitor, the method comprising:

(a) obtaining a prediction of a response of the patient diagnosed with NSCLC to a medicament selected from the group consisting of a PD-1 immune checkpoint inhibitor or a PD-L1 immune checkpoint inhibitor, wherein the obtaining comprises the steps of:

(i) measuring the kinase activity of at least one kinase of the vascular endothelial growth factor receptor (VEGFR) or platelet-derived growth factor receptor (PDGFR) family of kinases selected from the group consisting of: fms-like tyrosine kinase 1 (FLT1), fms-like tyrosine kinase 3 (FLT3) and fms-like tyrosine kinase 4 (FLT4);

at least one kinase of the proto-oncogene tyrosine-protein kinase Src (SRC) family of kinases selected from the group consisting of: SRC, B lymphocyte kinase (BLK), leukocyte C-terminal Src kinase (LCK), proto-onco-gene c-Fyn (FYN) and tyrosine-protein kinase Yes (YES);

and at least one kinase of the spleen tyrosine kinase (SYKyk) family of kinases selected from the group consisting of SYK and 70 kDa zeta-chain associated protein (ZAP70), in a blood sample comprising peripheral blood mononu-clear cells obtained from said patient, thereby provid-ing a kinase activity profile of said blood sample; and (ii) determining a response of said patient to said medi-cament from said kinase activity profile;

wherein the response of said patient to said medicament is determined from said kinase activity profile by:

comparing said kinase activity profile to a first and a second reference kinase activity profile; said first ref-erence kinase activity profile being representative of a good responder to said medicament and said second reference kinase activity profile being representative for a poor responder to said medicament; and determining a response of said patient to said medicament on the basis of the comparison of said kinase activity profile with said first and said second reference kinase activity profile; or wherein the response of said patient to said medicament is determined from said kinase activity profile by:

calculating a classifier parameter from said kinase activity profile; and determining the response of said patient to said medica-ment on the basis of said classifier parameter, wherein said classifier parameter being above a first predeter-mined threshold level indicates a good responder and said classifier parameter being below a second prede-termined threshold level indicates a poor responder;

wherein the kinase activity in step (i) is measured by contacting the blood sample from the patient with one or more protein kinase substrate(s) thereby generating one or more phosphorylation profile(s), and said kinase activity profile is determined from said phosphory-lation profile(s) using upstream kinase analysis; and (b) categorizing the patient as a good responder to said medicament, wherein said categorization is based on a level of kinase activity in said kinase activity profile of at least one kinase selected from FLT1, FLT3, FLT4, at least one kinase selected from SRC, BLK, LCK, FYN and YES, and at least one kinase of the selected from SYK and ZAP70 and (c) treating said patient found to be a good responder with the medicament.

2. The method according to claim 1, wherein said method further comprises measuring the kinase activity of Janus kinase 2 (JAK2), tyrosine kinase-type cell surface receptor HER4 (HER4) and/or tropomyosin-related kinase B (TRKB).

3. The method according to the claim 1, wherein said method comprises measuring the kinase activity of FLT1, FLT3, FLT4, SRC, BLK, LCK, FYN, YES, SYK, and ZAP70.

4. The method according to claim 1, wherein said medi-cament is selected from the group consisting of: Nivolumab, Pembrolizumab, Durvalumab, Atezolizumab, Avelumab and Cemiplimab.

5. The method according to claim 1, wherein in step (a) said kinase activity is determined by contacting the sample with at least one protein kinase substrate, thereby providing a phosphorylation profile of said sample, said phosphory-lation profile comprising the phosphorylation levels of phos-phorylation sites present in peptide markers with SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 and 93.

6. The method according to claim 1, wherein said NSCLC is a stage III or stage IV NSCLC.

7. The method according to claim 1, wherein susceptibil-ity of a patient having NSCLC to a PD-1 or PD-L1 immune checkpoint inhibitor is assessed.

8. The method according to claim 1, wherein a pharma-ceutical or clinical value of a PD-1 or PD-L1 immune checkpoint inhibitor is assessed.

9. The method according to claim 1, wherein the medi-cament is selected from Nivolumab or Pembrolizumab.

* * * * *